US009597669B2

(12) United States Patent
Spannhoff et al.

(10) Patent No.: US 9,597,669 B2
(45) Date of Patent: Mar. 21, 2017

(54) CATALYST AND PROCESS FOR THE CONVERSION OF OXYGENATES TO OLEFINS

(71) Applicant: BASF SE, Ludwigshafen (DE)

(72) Inventors: Kirsten Spannhoff, Lugwigshafen (DE); Florina Corina Patcas, Ludwigshafen (DE); Kerem Bay, Ludwigshafen (DE); Manuela Gaab, Heidelberg (DE); Ekkehard Schwab, Neustadt (DE); Michael Hesse, Worms (DE)

(73) Assignee: BASF SE, Ludwigshafen (DE)

( * ) Notice: Subject to any disclaimer, the term of this patent is extended or adjusted under 35 U.S.C. 154(b) by 586 days.

(21) Appl. No.: 13/927,839

(22) Filed: Jun. 26, 2013

(65) Prior Publication Data
US 2014/0005457 A1 Jan. 2, 2014

Related U.S. Application Data

(60) Provisional application No. 61/665,919, filed on Jun. 29, 2012.

(51) Int. Cl.
B01J 29/06 (2006.01)
C07C 1/20 (2006.01)
B01J 29/40 (2006.01)
B01J 38/02 (2006.01)
B01J 23/02 (2006.01)
B01J 23/10 (2006.01)
B01J 29/70 (2006.01)
B01J 29/80 (2006.01)
B01J 29/90 (2006.01)
B01J 35/04 (2006.01)
B01J 37/02 (2006.01)
B01J 37/28 (2006.01)
B01J 37/00 (2006.01)
C07C 11/04 (2006.01)
C07C 11/06 (2006.01)
C07C 11/08 (2006.01)

(52) U.S. Cl.
CPC ............ *B01J 29/40* (2013.01); *B01J 23/02* (2013.01); *B01J 23/10* (2013.01); *B01J 29/061* (2013.01); *B01J 29/70* (2013.01); *B01J 29/7038* (2013.01); *B01J 29/80* (2013.01); *B01J 29/90* (2013.01); *B01J 35/04* (2013.01); *B01J 37/0215* (2013.01); *B01J 38/02* (2013.01); *C07C 1/20* (2013.01); *B01J 37/0009* (2013.01); *B01J 37/28* (2013.01); *B01J 2229/186* (2013.01); *B01J 2229/20* (2013.01); *B01J 2229/42* (2013.01); *C07C 11/04* (2013.01); *C07C 11/06* (2013.01); *C07C 11/08* (2013.01); *C07C 2521/04* (2013.01); *C07C 2527/173* (2013.01); *C07C 2529/40* (2013.01); *C07C 2529/70* (2013.01); *Y02P 20/584* (2015.11)

(58) Field of Classification Search
USPC ......... 502/60, 63, 64, 77; 585/638, 639, 640
See application file for complete search history.

(56) References Cited

U.S. PATENT DOCUMENTS

| 4,049,573 | A | | 9/1977 | Kaeding | |
|---|---|---|---|---|---|
| 4,357,264 | A | * | 11/1982 | Chu | B01J 29/40 502/77 |
| 4,423,266 | A | * | 12/1983 | Young | B01J 29/40 208/135 |
| 4,433,189 | A | * | 2/1984 | Young | C07C 1/20 502/77 |
| 4,504,690 | A | | 3/1985 | Forbus et al. | |
| 4,548,914 | A | | 10/1985 | Chu | |
| 4,654,455 | A | * | 3/1987 | Chao | B01J 29/40 585/415 |
| 4,692,423 | A | | 9/1987 | Caesar | |
| 2002/0038775 | A1 | | 4/2002 | Sterte et al. | |
| 2007/0149384 | A1 | * | 6/2007 | Ghosh | B01J 29/40 502/60 |
| 2009/0048093 | A1 | | 2/2009 | Mizutani et al. | |
| 2013/0197288 | A1 | * | 8/2013 | Schafer | C07C 1/0425 585/324 |
| 2014/0005455 | A1 | | 1/2014 | Spannhoff et al. | |
| 2014/0005457 | A1 | | 1/2014 | Spannhoff et al. | |
| 2014/0058180 | A1 | | 2/2014 | Klingelhöfer et al. | |

FOREIGN PATENT DOCUMENTS

DE 238733 9/1986
DE 238733 A1 9/1986
(Continued)

OTHER PUBLICATIONS

Antia, J., et al., "Conversion of Methanol to Gasoline-Range Hydrocarbons in a ZSM-5 Coated Monolithic Reactior", Ind. Eng. Chem. Res., vol. 34, (1995) pp. 140-147.
(Continued)

Primary Examiner — Elizabeth Wood
(74) Attorney, Agent, or Firm — Drinker Biddle & Reath LLP

(57) ABSTRACT

The present invention relates to a catalyst for the conversion of oxygenates to olefins, wherein the catalyst comprises one or more zeolites of the MFI, MEL and/or MWW structure type and particles of one or more metal oxides, the one or more zeolites of the MFI, MEL and/or MWW structure type comprising one or more alkaline earth metals, and the particles of the one or more metal oxides comprising phosphorus, the phosphorus being present at least partly in oxidic form, and the one or more alkaline earth metals being selected from the group consisting of Mg, Ca, Sr, Ba and combinations of two or more thereof, to the preparation and use thereof, and to a process for converting oxygenates to olefins using the catalyst.

22 Claims, 3 Drawing Sheets

(56) References Cited

FOREIGN PATENT DOCUMENTS

| | | |
|---|---|---|
| EP | 2143700 | 1/2010 |
| JP | 2007/137840 | 6/2007 |
| WO | WO-94/25151 A1 | 11/1994 |
| WO | WO-98/29519 A1 | 7/1998 |
| WO | WO-2009/092779 | 7/2009 |
| WO | WO-2011/089263 | 7/2011 |
| WO | WO-2012/123556 | 9/2012 |
| WO | WO-2012/123557 | 9/2012 |
| WO | WO-2012/123558 | 9/2012 |
| WO | WO-2012123556 A1 | 9/2012 |
| WO | WO-2012123557 A1 | 9/2012 |
| WO | WO-2012123558 A1 | 9/2012 |
| WO | WO-2013/017497 | 2/2013 |
| WO | WO-2014/001410 | 1/2014 |
| WO | WO-2014/001411 | 1/2014 |
| WO | WO-2014/001412 | 1/2014 |

OTHER PUBLICATIONS

Ciambelli, P., "Acid-Base Catalysis in the Conversion of Methanol to Olefins Over Mg-Modified Zsm-5 Zeolite", Successful Design of Catalysis, (1988), pp. 239-246.

Frieding, J., et al., "Extrusion of zeolites: Properties of catalysts with a novel aluminium phosphate sintermatrix", Applied Catalysis A: General, vol. 328, (2007), pp. 210-218.

Goryainova, T., et al., "Study of Magnesium-Containing Zeolite Catalysts for the Synthesis of Lower Olefins from Dimethyl Ether", Petroleum Chemistry, vol. 51, No. 3, (2011), pp. 169-173.

Hammon, U., et al., "Formation of Ethene and Propene from Methanol on Zeolite ZSM-5, II. Preparation of Finished Catalysts and Operation of a Fixed-Bed Pilot Plant", Applied Catalysis, vol. 37, (1998), pp. 155-174.

Ivanova S., et al., "ZSM-5 Coatings on β-SiC Monoliths: Possible New Structured Catalyst for the Methanol-to-Olefins Process", J. Phys. Chem. C, vol. 111, (2007), pp. 4368-4374.

Lee, Y., et al., "Novel aluminophosphate (AlPO) bound ZSM-5 extrudates with improved catalytic properties for methanol to propylene (MTP) reaction", Applied Catalysis A: General, vol. 374, (2010), pp. 18-25.

Lee, Y., et al., "Textural Properties and Catalytic Applications of ZSM-5 Monolith Foam for Methanol Conversion", Catal Lett, vol. 129, (2009), pp. 408-415.

McIntosh, R., et al., "The Properties of Magnesium and Zinc Oxide Treated ZSM-5 Catalysts for Conversion of Methanol Into Olefin-Rich Products", Applied Catalysis, vol. 6, (1983), pp. 307-314.

Okado, H., et al., "Deactivation Resistance of ZSM-5-Type Zeolites containing Alkaline Earth Metals used for Methanol Conversion", Applied Catalysis, vol. 41, (1988), pp. 121-135.

Patcas, F., et al., "The methanol-to-olefins conversion over zeolite-coated ceramic foams", Journal of Catalysis, vol. 231, (2005) pp. 194-200.

International Search Report for PCT/EP2013/063434 mailed Jan. 20, 2014.

Yang, "Preparation of Modified ZSM-5/Cordierite Monolithic Catalyst and Their Catalytic Performance of Methanol to Olefin," Dissertation (2011), Executive Summary.

\* cited by examiner

CATALYST AND PROCESS FOR THE CONVERSION OF OXYGENATES TO OLEFINS

CROSS-REFERENCE TO RELATED APPLICATIONS

This application claims benefit (under 35 USC 119(e)) of U.S. Provisional Application 61/665,919, filed Jun. 29, 2012, which is incorporated by reference.

BACKGROUND OF THE INVENTION

The present invention relates to a catalyst for the conversion of oxygenates to olefins, and to a process for preparation thereof. The present invention further relates to a process for conversion of oxygenates to olefins, and to the use of a catalyst according to the present invention in specific catalytic processes.

INTRODUCTION

In view of increasing scarcity of mineral oil deposits which serve as starting material for preparation of lower hydrocarbons and derivatives thereof, alternative processes for preparing such commodity chemicals are becoming increasingly important. In alternative processes for obtaining lower hydrocarbons and derivatives thereof, specific catalysts are frequently used in order to obtain lower hydrocarbons and derivatives thereof, such as unsaturated lower hydrocarbons in particular, with maximum selectivity from other raw materials and/or chemicals. In this context, important processes include those in which methanol as a starting chemical is subjected to a catalytic conversion, which can generally give rise to a mixture of hydrocarbons and derivatives thereof, and also aromatics.

In the case of such catalytic conversions, it is a particular challenge to refine the catalysts used therein, and also the process regime and parameters thereof, in such a way that a few very specific products form with maximum selectivity in the catalytic conversion. Thus, these processes are named particularly according to the products which are obtained in the main therein. In the past few decades, particular significance has been gained by those processes which enable the conversion of methanol to olefins and are accordingly characterized as methanol-to-olefin processes (MTO process for methanol to olefins). For this purpose, there has been development particularly of catalysts and processes which convert methanol via the dimethyl ether intermediate to mixtures whose main constituents are ethene and propene.

DD 238733 A1 relates, for example, to a magnesium-doped zeolite and to the use thereof in the conversion of methanol to lower olefins, specifically of the carbon number range ≥3. McIntosh et al. in Applied Catalysis 1983, 6, p. 307-314 describes specifically ZSM-5 catalysts and the use thereof in methanol-to-olefin processes, and the doping thereof with various metals and nonmetals, for example magnesium or phosphorus, and the influence thereof on the yields and product distribution in the catalytic conversion of methanol.

Lee et al. in Applied Catalysis A 2010, 374, p. 18-25 relates to ZSM-5 extrudates with aluminophosphate binder and to the use thereof in methanol-to-propylene processes (MTP processes). Freiding et al. in Applied Catalysis A 2007, 328, p. 210-218 describes extrudates of ZSM-5 in an aluminophosphate sinter matrix.

U.S. Pat. No. 4,049,573 relates to a catalytic process for conversion of lower alcohols and ethers thereof, and especially methanol and dimethyl ether, selectively to a hydrocarbon mixture with a high proportion of C2-C3 olefins and monocyclic aromatics and especially para-xylene, the catalysts used therein being doped with boron, magnesium and/or phosphorus.

Goryainova et al. in Petroleum Chemistry 2011, vol. 51, no. 3, p. 169-173 describes the catalytic conversion of dimethyl ether to lower olefins using magnesium-containing zeolites.

Ciambelli et al. "Acid-base catalysis in the conversion of methanol to olefins over Mg-modified ZSM-5 zeolite", Successful Design of Catalysts, Elsevier Science Publishers B.V., Amsterdam, 1988, p. 239-246 examines the influence of magnesium in the MTO process and especially in combination with ZSM-5 zeolite as a catalyst.

Okado et al. in Applied Catalysis 1988, 41, p. 121-135 relates to methanol-to-olefin processes using the ZSM-5 catalyst and examines the influence of various alkaline earth metals with regard to deactivation of the catalyst during the service life thereof.

WO 2012/123556 A1 relates to a catalyst which is produced by mixing a zeolite of the pentasil type which has been modified by a first phosphorus compound with alumina and an acid and processing the mixture to give a shaped body, which is then impregnated with a second phosphorus compound. WO 2012/123558 A1 describes a catalyst which is produced by impregnating a zeolite-containing shaped body with a phosphorus compound, the zeolite being of the pentasil type. Finally, WO 2012/123557 A1 relates to a catalyst which is prepared by mixing a zeolite of the pentasil type, which has first been modified by a phosphorus compound which is then substantially removed again from the zeolite, with alumina and an acid, and processing the mixture to give a shaped body.

In spite of the advances which have been achieved with respect to the selectivities of different catalysts in processes for preparing lower hydrocarbons and derivatives thereof, this covers only a portion of the possible products. Thus, there is still a need for new processes and catalysts which can have high selectivities with respect to particular products and product mixtures, especially with respect to the olefins of different chain length which are obtained in such processes. Irrespective of this, there is still a general need for new catalysts and processes which, as well as new and/or improved selectivities, also have better resistance to any deactivation in such processes, especially as a result of coking of the catalyst, in order thus to be able to enable a higher efficiency of existing and new processes.

A SUMMARY OF THE INVENTION

A catalyst for the conversion of oxygenates to olefins, wherein the catalyst comprises one or more zeolites of the MFI, MEL and/or MWW structure type and particles of one or more metal oxides, the one or more zeolites of the MFI, MEL and/or MWW structure type comprising one or more alkaline earth metals, and the particles of the one or more metal oxides comprising phosphorus, the phosphorus being present at least partly in oxidic form, and the one or more alkaline earth metals being selected from the group consisting of Mg, Ca, Sr, Ba and combinations of two or more thereof.

DETAILED DESCRIPTION

Figure 1:
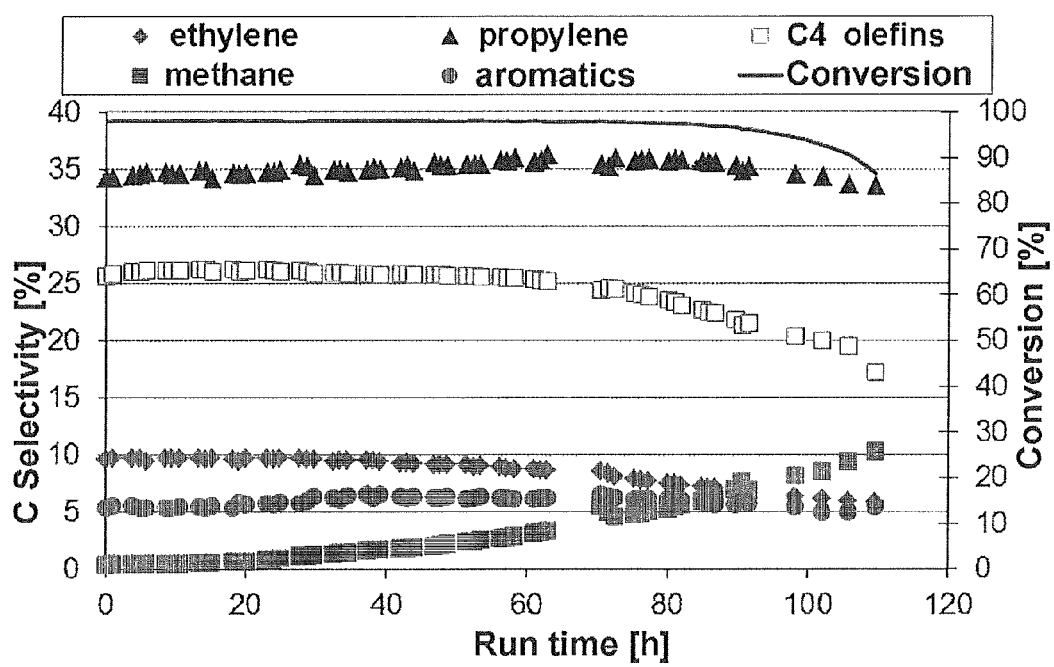
FIG. 1 shows the methanol conversion and the respective ethylene, propylene, C4 olefin, C4 paraffin and methane selectivities of the catalyst according to example 1 in the MTO test according to example 3 as a function of run time. The abscissa axis represents the service life in hours, the left-hand ordinate axis the selectivity in % for ethylene (measurement points: "♦"), propylene (measurement points: "▲"), C4 olefin (measurement points: "□"), aromatics (measurement points: "●"), and methane (measurement points: "■"), and the right-hand ordinate axis the methanol or dimethyl ether conversion in % which is shown in the graph as a continuous line.

It was thus an object of the present invention to provide an improved catalyst, especially for the conversion of oxygenates to olefins, which has new and improved selectivities with respect to particular process products. More particularly, it was an object of the present invention to provide improved catalysts and processes for the conversion of oxygenates to olefins, which exhibit a specific selectivity with respect to C3 and C4 olefins. It was an additional object of the present invention to provide catalysts and processes which enable a longer service life of the catalyst with comparable space velocity and conversion of oxygenates. It was a further object of the present invention to provide an improved catalyst which produces a lower level of unwanted by-products, and especially an improved catalyst and a process for the conversion of oxygenates to olefins using the latter, which produces a smaller amount of lightweight gases such as methane, ethane and propane, and especially a smaller amount of methane, as an unwanted by-product of the reaction.

It has thus been found that, surprisingly, a catalyst for the conversion of oxygenates to olefins, which contains a phosphorus-doped metal oxide in addition to a zeolite of the MFI, MEL and/or MWW structure type comprising one or more alkaline earth metals not only exhibits a surprisingly high selectivity with respect to C3 and C4 olefins, but unexpectedly also possesses a considerably improved service life. More particularly, it has been found that, unexpectedly, a synergistic effect of the doping of one or more zeolites with one or more alkaline earth metals in combination with the doping of a metal oxide used especially as a binder with phosphorus can be achieved, both with respect to the olefin selectivity in the case of use of the catalyst for conversion of oxygenates and with respect to a considerable improvement in the resistance of the catalyst to deactivation during the use thereof in a catalytic process. Furthermore, it has been found that, surprisingly, in addition to the above-described advantages, a synergistic effect is also observed in that the amount of unwanted by-products and especially of methane in the conversion of oxygenates is considerably and sustainably reduced by the combination of the doping of one or more zeolites with one or more alkaline earth metals with the doping of a metal oxide used especially as a binder with phosphorus.

Thus, the present invention relates to a catalyst for the conversion of oxygenates to olefins, wherein the catalyst comprises one or more zeolites of the MFI, MEL and/or MWW structure type and particles of one or more metal oxides, the one or more zeolites of the MFI structure type comprising one or more alkaline earth metals, and the particles of the one or more metal oxides comprising phosphorus, the phosphorus being present at least partly in oxidic form, and the one or more alkaline earth metals being selected from the group consisting of Mg, Ca, Sr, Ba and combinations of two or more thereof.

With regard to the one or more zeolites present in the catalyst, according to the present invention, there are no restrictions whatsoever either with respect to the type or with respect to the number of zeolites which can be used herein, provided that they are zeolites of one or more of the MFI, MEL and MWW structure types. If one or more of the zeolites present in the catalyst are of the MWW structure type, there is again no restriction whatsoever with respect to the type and/or number of MWW zeolites which can be used according to the present invention. Thus, these may be selected, for example, from the group of zeolites of the MWW structure type consisting of MCM-22, [Ga—Si—O]-MWW, [Ti—Si—O]-MWW, ERB-1, ITQ-1, PSH-3, SSZ-25 and mixtures of two or more thereof, preference being given to the use of zeolites of the MWW structure type which are suitable for the conversion of oxygenates to olefins, especially MCM-22 and/or MCM-36.

The same applies correspondingly to the zeolites of the MEL structure type which can be used according to the present invention in the catalyst, these being selected, for example, from the group consisting of ZSM-11, [Si—B—O]-MEL, boron-D (MFI/MEL mixed crystal), boralite D, SSZ-46, silicalite 2, TS-2 and mixtures of two or more thereof. Here too, preference is given to using those zeolites of the MEL structure type which are suitable for the conversion of oxygenates to olefins, especially [Si—B—O]-MEL.

According to the present invention, however, especially zeolites of the MFI structure type are used in the inventive catalyst for the conversion of oxygenates to olefins. With regard to these preferred embodiments of the present invention, there is likewise no restriction whatsoever with respect to the type and/or number of the zeolites of this structure type used, the one or more zeolites of the MFI structure type which are used in the inventive catalyst preferably being selected from the group consisting of ZSM-5, ZBM-10, [Fe—Si—O]-MFI, [Ga—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof. Further preferably, according to the present invention, the catalyst comprises ZSM-5 and/or ZBM-10 as the zeolite of the MFI structure type, particular preference being given to using ZSM-5 as the zeolite. With regard to the zeolitic material ZBM-10 and the preparation thereof, reference is made, for example, to EP 0 007 081 A1 and to EP 0 034 727 A2, the content of which, particularly with regard to the preparation and characterization of the material, is hereby incorporated into the present invention.

Thus, according to the present invention, preference is given to embodiments of the catalyst for the conversion of oxygenates to olefins in which the one or more zeolites are of the MFI structure type, and are preferably selected from the group consisting of ZSM-5, ZBM-10, [Fe—Si—O]-MFI, [Ga—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof, further preferably from the group consisting of ZSM-5, ZBM-10 and mixtures thereof, the zeolite of the MFI structure type preferably being ZSM-5.

In a preferred embodiment of the present invention, the catalyst does not comprise any significant amounts of one or more nonzeolitic materials and especially does not comprise any significant amounts of one or more aluminophosphates (AlPOs or APOs) or of one or more aluminosilicophosphates (SAPOs). In the context of the present invention, the catalyst is essentially free of or does not comprise any significant amounts of a specific material in cases in which this specific material is present in the catalyst in an amount of % by weight or less based on 100% by weight of the total amount of the one or more zeolites of the MFI, MEL and/or MWW structure type, preferably in an amount of 0.5% by weight or less, further preferably of 0.1% by weight or less, further preferably of 0.05% by weight or less, further preferably of 0.001% by weight or less, further preferably of 0.0005% by weight or less and further preferably in an amount of 0.0001% by weight or less. A specific material in the context of the present invention particularly denotes a particular element or a particular combination of elements, a particular substance or a particular substance mixture, and also combinations and/or mixtures of two or more thereof.

The aluminophosphates (AlPOs and APOs) in the context of the present invention generally include all crystalline aluminophosphate phases. According to a preferred definition of the aluminophosphates (AlPOs and APOs), these include the materials AlPO-20 and composition variants thereof, AlPO-5, AlPO-21, AlPO-H3, AlPO-17 and composition variants thereof, AlPO-12-TAMU, AlPO-11, AlPO-22, AlPO-8, AlPO-C, AlPO-25, AlPO-16, AlPO-31, AlPO-8, AlPO-H2, AlPO-31, AlPO-34, AlPO-D, AlPO-18, AlPO-EN3, AlPO-53(A), AlPO-41, AlPO-52, AlPO4-pollucite, AlPO-24, AlPO-C, AlPO-33, AlPO-17 and composition variants thereof, AlPO-20 and composition variants thereof, AlPO-H2, AlPO-14, AlPO-54, AlPO-53(B), AlPO-40, AlPO-35, AlPO-CJB1 (optionally with additional presence of phosphate groups), AlPO-40, AlPO-36, MnAPO-11, MAPO-43, CoAPO-5, MAPO-36, MgAPO-50, ZAPO-M1, GaPO-DAB-2, CrAPO-5, CoAPO-50, MAPO-39, CoAPO-44, GaPO-34, MeAPO-47, GaPO-DAB-2, CoAPO-47, MeAPO-47, GaPO-14, CoAPO-50, CFSAPO-1A, GeAPO-11, CoAPO-5, MAPO-5 (where M=Mg, Mn), VAPO-5, ZnAPO-5, FAPO-5, MnAPO-41, CoAPO-40, ZnAPO-40, MAPO-46, MnAPO-50, CoAPO-H3, ZnAPO-39, MAPO-31 (where M=Zn, Mg, Mn, Co, Cr, Cu, Cd), ZnAPO-36, ZnAPO-35, FAPO-H1, MnAPO-14, ZnAPO-50, AlPO-CJ3, FAPO-36, MAPO-31 (where M=Mn, Ni, Zn), VAPO-31, MAPO-5 (where M=Cd, Cu, Mo, V/Mo, Zr) and CoAPO-CJ40. According to a preferred definition of the aluminophosphates (AlPOs and APOs), these include all crystalline aluminophosphate phases which consist of aluminum, phosphorus and oxygen, and especially the materials AlPO-5, AlPO-21, AlPO-H3, AlPO-17 and composition variants thereof, AlPO-12-TAMU, AlPO-11, AlPO-22, AlPO-8, AlPO-C, AlPO-25, AlPO-16, AlPO-31, AlPO-8, AlPO-H2, AlPO-31, AlPO-34, AlPO-D, AlPO-18, AlPO-EN3, AlPO-53(A), AlPO-41, AlPO-52, AlPO4-pollucite, AlPO-24, AlPO-C, AlPO-33, AlPO-17 and composition variants thereof, AlPO-20 and composition variants thereof, AlPO-H2, AlPO-14, AlPO-54, AlPO-53(B), AlPO-40, AlPO-35, AlPO-CJB1 (optionally with additional presence of phosphate groups), AlPO-40 and AlPO-36.

The aluminosilicophosphates (SAPOs) in the context of the present invention generally include all crystalline aluminosilicophosphate phases, especially the SAPO materials SAPO-11, SAPO-47, SAPO-40, SAPO-43, SAPO-5, SAPO-31, SAPO-34, SAPO-37, SAPO-35, SAPO-42, SAPO-56, SAPO-18, SAPO-41, SAPO-39 and CFSAPO-1A.

According to the present invention, the one or more zeolites of the MFI, MEL and/or MWW structure type comprises one or more alkaline earth metals selected from the group consisting of Mg, Ca, Sr, Ba and combinations of two or more thereof. In general, according to the present invention, there is no restriction whatsoever either with regard to the type and/or the number of alkaline earth metals present in the one or more zeolites, or with regard to the manner in which they are present in the one or more zeolites, provided that the one or more zeolites comprise one or more alkaline earth metals selected from the group consisting of magnesium, calcium, strontium, barium and combinations of two or more thereof. According to the present invention, the one or more alkaline earth metals, however, are preferably selected from the group consisting of magnesium, calcium, strontium and combinations of two or more thereof, and, in particularly preferred embodiments of the inventive catalyst, the alkaline earth metal is magnesium. In alternatively preferred embodiments of the present invention, the catalyst does not comprise any, or any significant amounts of, calcium and/or strontium.

Thus, according to the present invention, preference is given to embodiments of the catalyst for the conversion of oxygenates to olefins in which the alkaline earth metals present in the one or more zeolites of the MFI, MEL and/or MWW structure type are selected from the group consisting of Mg, Ca, Sr and combinations of two or more thereof, the alkaline earth metal more preferably being Mg.

With regard to the manner in which the one or more alkaline earth metals are present in the one or more zeolites in the catalyst, these may in principle be present in the micropores of the one or more zeolites and/or as a constituent of the zeolitic skeleton, especially at least partly in isomorphic substitution for an element in the zeolite skeleton, preferably for silicon and/or aluminum as a constituent of the zeolite skeleton and more preferably at least partly in isomorphic substitution for aluminum. With regard to the presence of the one or more alkaline earth metals in the micropores of the one or more zeolites, these may be present as a separate compound, for example as a salt and/or oxide therein, and/or as a positive counterion to the zeolite skeleton. According to the present invention, the one or more alkaline earth metals are present at least partly in the pores and preferably in the micropores of the one or more zeolites, and, further preferably, the one or more alkaline earth metals are present therein at least partly as the counterion of the zeolite skeleton, as can arise, for example, in the course of production of the one or more zeolites in the presence of the one or more alkaline earth metals and/or can be brought about by performance of an ion exchange with the one or more alkaline earth metals in the zeolite already produced.

With regard to the amount of the one or more alkaline earth metals, as already noted above, there are no particular restrictions according to the present invention with respect to the amount in which they are present in the one or more zeolites. It is thus possible in principle for any possible amount of the one or more alkaline earth metals to be present in the one or more zeolites, for example in a total amount of the one or more alkaline earth metals of 0.1-20% by weight based on the total amount of the one or more zeolites. According to the present invention, however, it is preferred that the one or more alkaline earth metals are present in a total amount in the range of 0.5-15% by weight based on 100% by weight of the total amount of the one or more zeolites, further preferably of 1-10% by weight, further preferably of 2-7% by weight, further preferably of 3-5% by weight and further preferably of 3.5-4.5% by weight. In particularly preferred embodiments of the present invention, the one or more alkaline earth metals are present in a total amount in the range of 3.8-4.2% by weight in the one or more zeolites. For all of the above percentages by weight for alkaline earth metal in the one or more zeolites, these are calculated proceeding from the one or more alkaline earth metals as the metal.

Thus, according to the present invention, preference is given to embodiments of the catalyst for the conversion of oxygenates to olefins in which the one or more zeolites of the MFI, MEL and/or MWW structure type comprise the one or more alkaline earth metals in a total amount in the range from 0.1 to 20% by weight, preferably from 0.5 to 15% by weight, further preferably from 1 to 10% by weight, further preferably from 2 to 7% by weight, further preferably from 3 to 5% by weight, further preferably from 3.5 to 4.5% by weight, and further preferably in the range from 3.8 to 4.2% by weight, based in each case on the total amount of the one or more zeolites of the MFI, MEL and/or MWW structure type and calculated as the metal. In alternatively preferred embodiments of the inventive catalyst, the one or more zeolites of the MFI, MEL and/or MWW structure type comprise the one or more alkaline earth metals in a total amount in the range from 0.1 to 10% by weight, further preferably from 0.5 to 5% by weight, further preferably from 0.8 to 3% by weight, further preferably from 1 to 2.5% by weight, further preferably from 1.2 to 2.2% by weight, and further preferably in the range from 1.6 to 2.0% by weight, based in each case on the total amount of the one or more zeolites of the MFI, MEL and/or MWW structure type and calculated as the metal.

According to the present invention, the catalyst for the conversion of oxygenates to olefins comprises, as well as the above-described zeolites, especially according to the particular and preferred embodiments as described in the present application, further particles of one or more metal oxides. According to the present invention, there are no restrictions whatsoever either with respect to the type metal oxides which may be used in the catalyst, or with respect to the number of different metal oxides which may be present therein. According to the present invention, however, preference is given to metal oxides which are generally used in catalytic materials as inert materials and especially as support substances, preferably with a large BET surface area. According to the present invention, figures for surface areas of a material are preferably based on the BET (Brunauer-Emmett-Teller) surface area thereof, this preferably being determined to DIN 66131 by nitrogen absorption at 77 K.

With regard to the metal oxides which can be used in the present invention, there are no restrictions whatsoever. It is thus possible in principle to use any suitable metal oxide compound and mixtures of two or more metal oxide compounds. Preference is given to using metal oxides which are thermally stable in processes for the conversion of oxygenates to olefins, the metal oxides preferably serving as binders. Thus, the one or more metal oxides which are used in the catalyst are preferably selected from the group consisting of alumina, titania, zirconia, aluminum-titanium mixed oxides, aluminum-zirconium mixed oxides, aluminum-lanthanum mixed oxides, aluminum-zirconium-lanthanum mixed oxides, titanium-zirconium mixed oxides and mixtures of two or more thereof. Further preferably, according to the present invention, the one or more metal oxides are selected from the group consisting of alumina, aluminum-titanium mixed oxides, aluminum-zirconium mixed oxides, aluminum-lanthanum mixed oxides, aluminum-zirconium-lanthanum mixed oxides and mixtures of two or more thereof. According to the present invention, particular preference is given to using the metal oxide alumina as particles in the catalyst.

According to the present invention, it is further preferred that the metal oxide is at least partly in amorphous form. In particular embodiments of the present invention, according to which the metal oxide is used at least partly in crystalline form, it is preferred that the phosphorus present in the metal oxide is not present therein as part of the crystal structure of the metal oxide and hence does not form an element or part of the crystal structure that would at least partly require crystallinity of the metal oxide. More particularly, according to the present invention, it has been found that, surprisingly, specifically in combination with one or more alkaline earth metal-comprising zeolites according to the present invention, the application of phosphorus to a metal oxide as a binder in a process for the conversion of oxygenates to olefins not only effectively suppresses the formation of coke on the catalyst, as a result of which the service life can be considerably prolonged, but also, unexpectedly, considerably and sustainably reduces the formation of unwanted by-products and especially of methane.

Thus, according to the present invention, preference is given to embodiments of the catalyst for the conversion of oxygenates to olefins in which the one or more metal oxides are selected from the group consisting of alumina, titania, zirconia, aluminum-titanium mixed oxides, aluminum-zirconium mixed oxides, aluminum-lanthanum mixed oxides, aluminum-zirconium-lanthanum mixed oxides, titanium-zirconium mixed oxides and mixtures of two or more thereof, preferably from the group consisting of alumina, aluminum-titanium mixed oxides, aluminum-zirconium mixed oxides, aluminum-lanthanum mixed oxides, aluminum-zirconium-lanthanum mixed oxides and mixtures of two or more thereof, the metal oxide more preferably being alumina.

According to the present invention, the particles of the one or more metal oxides and especially of the one or more metal oxides according to the particular and preferred embodiment as described in the present application comprise phosphorus. With respect to the form in which the phosphorus is present in the particles of the one or more metal oxides, according to the present invention, there is no particular restriction whatsoever, provided that at least a portion of the phosphorus is in oxidic form. According to the present invention, phosphorus is in oxidic form if it is in present in conjunction with oxygen, i.e. if at least a portion of the phosphorus is at least partly in a compound with oxygen, especially with covalent bonding of at least a portion of the phosphorus to the oxygen. According to the present invention, it is preferred that the phosphorus which is at least partly in oxidic form comprises oxides of phosphorus and/or oxide derivatives of phosphorus. The oxides of phosphorus according to the present invention include especially phosphorus trioxide, diphosphorus tetroxide, phosphorus pentoxide and mixtures of two or more thereof. In addition, according to the present invention, it is preferred that the phosphorus and especially the phosphorus in oxidic form is at least partly in amorphous form, the phosphorus and especially the phosphorus in oxidic form further preferably being present essentially in amorphous form. According to the present invention, the phosphorus and especially the phosphorus in oxidic form is essentially in amorphous form when the proportion of phosphorus and especially of phosphorus in oxidic form which is present in crystalline form in the catalyst is 1% by weight or less based on 100% by weight of the total amount of the particles of the one or more metal oxides, the phosphorus being calculated as the element, preferably in an amount of 0.5% by weight or less, further preferably of 0.1% by weight or less, further preferably of 0.05% by weight or less, further preferably of 0.001% by weight or less, further preferably of 0.0005% by weight or less and further preferably in an amount of 0.0001% by weight or less.

With regard to the manner in which the phosphorus which is at least partly in oxidic form is present in the one or more metal oxides of the catalyst, according to the present invention, there is no particular restriction whatsoever, either with respect to the manner in which it is present, or with respect to the amount of phosphorus present in the one or more metal oxides. With respect to the manner in which the phosphorus is present, it may thus in principle be applied to the one or more metal oxides as the element and/or as one or more independent compounds and/or incorporated in the one or more metal oxides, for example in the form of a dopant of the one or more metal oxides, this especially comprising embodiments in which the phosphorus and the one or more metal oxides at least partly form mixed oxides and/or solid solutions. According to the present invention, the phosphorus is preferably applied partly in the form of one or more oxides and/or oxide derivatives to the one or more metal oxides in the particles, the one or more oxides and/or oxide derivatives of phosphorus further preferably originating from a treatment of the one or more metal oxides with one or more acids of phosphorus and/or with one or more of the salts thereof. The one or more acids of phosphorus preferably refer to one or more acids selected from the group consisting of phosphinic acid, phosphonic acid, phosphoric acid, peroxophosphoric acid, hypodiphosphonic acid, diphosphonic acid, hypodiphosphoric acid, diphosphoric acid, peroxodiphosphoric acid and mixtures of two or more thereof. Further preferably, the one or more phosphoric acids are selected from the group consisting of phosphonic acid, phosphoric acid, diphosphonic acid, diphosphoric acid and mixtures of two or more thereof, further preferably from the group consisting of phosphoric acid, diphosphoric acid and mixtures thereof, and, in particularly preferred embodiments of the present invention, the phosphorus present in the one or more metal oxides at least partly originates from a treatment of the one or more metal oxides with phosphoric acid and/or with one or more phosphate salts.

In a further embodiment which is preferred according to the present invention, the one or more zeolites of the MFI, MEL and/or MWW structure type likewise comprise phosphorus. With regard to the form in which the phosphorus is present in the one or more zeolites, the same applies as described in the present application with respect to phosphorus present in the one or more metal oxides, especially with regard to the partial presence thereof in oxidic form. With respect to the manner in which the phosphorus is present in the one or more zeolites, according to the present invention, it is preferably present in the pores of the zeolite skeleton and especially in the micropores thereof, either as an independent phosphorus-comprising compound and/or as a counterion to the zeolite skeleton, the phosphorus more preferably being present at least partly as an independent compound in the pores of the zeolite skeleton.

Thus, according to the present invention, preference is given to embodiments of the catalyst for the conversion of oxygenates to olefins in which the one or more zeolites of the MFI, MEL and/or MWW structure type comprise phosphorus, the phosphorus being at least partly in oxidic form.

With regard to the ratio in which the one or more zeolites of the MFI, MEL and/or MWW structure type on the one hand and the particles of one or more metal oxides on the other hand are present in the catalyst according to the present invention, there is no particular restriction in principle, the ratio preferably corresponding to one suitable for the use of the catalyst in at least one of the preferred inventive uses of the catalyst according to the particular and preferred uses as described in the present application, and especially a use for the conversion of oxygenates to olefins. Thus, the weight ratio of zeolite to metal oxide in the catalyst according to the present invention and especially according to the particular and preferred embodiments of the present invention may be in the range from 10:90 to 95:5. According to the present invention, the zeolite:metal oxide weight ratio, however, is preferably in the range from 20:80 to 90:10, further preferably in the range from 40:60 to 80:20 and further preferably in the range from 50:50 to 70:30. In particularly preferred embodiments of the present invention, the zeolite:metal oxide weight ratio is in the range from 55:45 to 65:45. In the context of the present invention, the zeolite:metal oxide weight ratio indicates especially the weight ratio of the total weight of the one or all of the plurality of zeolites to the total weight of the particles of the one or all of the plurality of metal oxides.

Thus, according to the present invention, preference is given to embodiments of the catalyst for the conversion of oxygenates to olefins in which the zeolite:metal oxide weight ratio in the catalyst is in the range from 10:90 to 95:5, preferably in the range from 20:80 to 90:10, further preferably in the range from 40:60 to 80:20, further preferably in the range from 50:50 to 70:30, and further preferably in the range from 55:45 to 65:45.

With regard to the amount of phosphorus which may be present in the catalyst according to the present invention, there is no restriction whatsoever in principle, and so all conceivably possible phosphorus contents may be present in the catalyst, these preferably being selected such that the catalyst can be used in at least one of the particular or preferred catalytic uses as described in the present application and especially for the conversion of oxygenates to olefins. Thus, the total amount of phosphorus in the catalyst according to the present invention may, for example, be in the range of 0.1-20% by weight, the total amount of phosphorus being based on the sum of the total weight of zeolites of the MFI, MEL and/or MWW structure type and the total weight of the particles of the one or more metal oxides, the phosphorus being calculated as the element. According to the present invention, the total amount of phosphorus in the catalyst, however, is preferably in the range of 0.5-15% by weight, further preferably in the range of 1-10% by weight, further preferably of 2-7% by weight, further preferably of 2.5-5% by weight, further preferably of 3.5-4.5% by weight, further preferably of 3.3-4.2% by weight and further preferably of 3.5-4% by weight. In particularly preferred embodiments of the present invention, the total amount of phosphorus in the catalyst based on the sum of the total weight of zeolites and the total weight of the particles of the one or more metal oxides is in the range of 3.7-3.9% by weight, the phosphorus being calculated as the element.

Thus, according to the present invention, preference is given to embodiments of the catalyst for the conversion of oxygenates to olefins in which the total amount of phosphorus, based on the sum of the total weight of zeolites of the MFI, MEL and/or MWW structure type and the total weight of the particles of the one or more metal oxides and calculated as the element, is in the range from 0.1 to 20% by weight, preferably from 0.5 to 15% by weight, further preferably from 1 to 10% by weight, further preferably from 2 to 7% by weight, further preferably from 2.5 to 5% by weight, further preferably from 3 to 4.5% by weight, further preferably from 3.3 to 4.2% by weight, further preferably from 3.5 to 4% by weight, and further preferably in the range from 3.7 to 3.9% by weight.

With regard to the form in which the catalyst according to the present invention is present, there are likewise no restrictions whatsoever, and so the one or more zeolites and the particles of the one or more metal oxides present therein may in principle be combined in any possible and suitable manner to give a catalyst, the form preferably being selected such that the catalyst is suitable at least in one of the particular or preferred uses as described in the present application and especially for the use of a catalyst for converting oxygenates to olefins. In this context, the catalyst is preferably in the form of a shaped body comprising a mixture of the one or more zeolites of the MFI, MEL and/or MWW structure type and the particles of the one or more metal oxides, preferably of the one or more zeolites and the particles of the one or more metal oxides according to one of the particular or preferred embodiments as described in the present application. In a particularly preferred embodiment of the present invention, the shaped body is an extrudate.

Thus, according to the present invention, preference is given to embodiments of the catalyst for the conversion of oxygenates to olefins in which the catalyst, and especially the catalyst according to one of the particular and preferred embodiments of the present invention, is in the form of a shaped body comprising a mixture of the one or more zeolites of the MFI, MEL and/or MWW structure type and of the particles of the one or more metal oxides.

The catalyst according to the present invention can be prepared in any suitable manner, provided that it comprises one or more zeolites of the MFI, MEL and/or MWW structure type and particles of one or more metal oxides according to the present invention and especially according to one of the particular or preferred embodiments of the invention as described in the present application. Preference is given to preparing the catalyst in the form of a shaped body comprising a mixture of the one or more zeolites of the MFI, MEL and/or MWW structure type and the particles of the one or more metal oxides according to the present invention and especially according to one of the particular or preferred embodiments as described in the present application with respect to the one or more zeolites and/or the particles of the one or more metal oxides.

Thus, the present invention also relates to a process for preparing a catalyst according to the present invention, and especially a catalyst according to one of the particular or preferred embodiments thereof, comprising (i) providing the one or more zeolites of the MFI, MEL and/or MWW structure type;
(ii) impregnating the one or more zeolites of the MFI, MEL and/or MWW structure type with a solution comprising the one or more alkaline earth metals, preferably by means of spray impregnation;
(iii) optionally drying the one or more impregnated zeolites obtained in (ii);
(iv) optionally calcining the one or more impregnated zeolites obtained in (ii) or (iii);
(v) preparing a mixture comprising the one or more impregnated and optionally dried and/or calcined zeolites of the MFI, MEL and/or MWW structure type, one or more solvents and particles of the one or more metal oxides and/or precursor compounds of the one or more particles of the one or more metal oxides;
(vi) homogenizing the mixture obtained in (v);
(vii) extruding the homogenized mixture obtained in (vi);
(viii) optionally drying the extrudate obtained in (vii);
(ix) optionally calcining the extrudate obtained in (vii) or (viii);
(x) impregnating the optionally dried and/or calcined extrudate with a phosphorus-comprising solution, preferably with phosphoric acid;
(xi) optionally drying the impregnated extrudate obtained in (x);
(xii) optionally calcining the extrudate obtained in (x) or (xi).

In addition, the present invention relates alternatively to a process for preparing a catalyst according to the present invention, and more particularly a catalyst according to one of the particular or preferred embodiments thereof, comprising (i) providing the one or more zeolites of the MFI, MEL and/or MWW structure type;
(ii) impregnating the one or more zeolites of the MFI, MEL and/or MWW structure type with a solution comprising the one or more alkaline earth metals, preferably by means of spray impregnation;
(iii) optionally drying the one or more impregnated zeolites obtained in (ii);
(iv) optionally calcining the one or more impregnated zeolites obtained in (ii) or (iii);
(v.1) preparing a mixture comprising the one or more impregnated and optionally dried and/or calcined zeolites of the MFI, MEL and/or MWW structure type and particles of the one or more metal oxides and/or precursor compounds of the one or more particles of the one or more metal oxides;
(v.2) admixing the mixture obtained in (v.1) with a phosphorus-comprising solution, preferably with one or more acids of phosphorus, more preferably with phosphoric acid;
(v.3) mixing the mixture obtained in (v.2) with one or more solvents;
(vi) homogenizing the mixture obtained in (v.3);
(vii) extruding the homogenized mixture obtained in (vi);
(viii) optionally drying the extrudate obtained in (vii);
(ix) optionally calcining the extrudate obtained in (vii) or (viii).

In the process according to the invention for preparing a catalyst according to the present invention, it is thus possible in principle to introduce phosphorus into the one or more metal oxides by the production of a metal oxide-comprising extrudate and the subsequent impregnation thereof with a phosphorus-comprising solution. In the alternative process for preparing a catalyst according to the present invention, phosphorus can be introduced as early as during the production of the extrudate, specifically by admixing the one or more metal oxides or precursor compounds thereof. Compared to the former process, the alternative process has the advantage that a catalyst according to the present invention can be obtained directly as an extrudate in (vii), whereas an inventive catalyst in the former process is not obtained until after an additional impregnation step (x) with a phosphorus-comprising solution.

With regard to the form in which the one or more zeolites of the MFI, MEL and/or MWW structure type is provided in step (i), there is no restriction whatsoever in principle, especially with respect to the further elements or compounds which may be present therein. Thus, there are generally no restrictions whatsoever with regard to the ions and compounds which may be present in the micropores of the one or more zeolites, especially with respect to the counterions to the possibly negatively charged zeolite skeleton which are present in the micropores. Accordingly, the one or more zeolites may be in a form in which the possibly negative charge of the zeolite skeleton is compensated for by one or more different cationic elements and/or compounds, this preferably being accomplished at least partly by means of one or more cationic elements and/or compounds selected from the group consisting of $H^+$, $NH_4^+$, $Li^+$, $Na^+$, $K^+$ and combinations of two or more thereof, further preferably from the group consisting of $H^+$, $Na^+$, $K^+$ and combinations of two or more thereof. In particularly preferred embodiments of the present invention, the one or more zeolites of the MFI, MEL and/or MWW structure type optionally comprise $H^+$ and/or $Na^+$, and preferably $H^+$ as the counterion to the negatively charged zeolite skeleton, which means that the one or more zeolites of the MFI, MEL and/or MWW structure type are more preferably provided in the respective H form thereof in step (i) of the process according to the invention.

In the particularly preferred embodiments of the present invention according to which the one or more zeolites of the MFI, MEL and/or MWW structure type in step (i) are each provided at least partly in the H form thereof, these can be converted to the desired H form by corresponding ion exchange. In the preferred embodiments of the process for preparing the catalyst according to which the one or more zeolites for the provision in (i) are optionally converted to the H form, there are no particular restrictions in principle with respect to the manner in which this is conducted, the conversion of the one or more zeolites preferably being effected by ion exchange. With respect to the preferred embodiments of the process for preparing the catalyst according to which the conversion of the one or more zeolites of the MFI, MEL and/or MWW structure type to the H form is effected over one or more ion exchange steps for the provision in step (i), there are again no particular restrictions with respect to the manner in which this is conducted, provided that at least some of the counterions to the zeolite skeleton can be exchanged for $H^+$ ions. In preferred embodiments, for the purpose of ion exchange, the one or more zeolites are contacted with a solution of a protonated volatile base, preferably of a protonated volatile amine, more preferably with an ammonium salt solution, or alternatively with an acid and preferably with an aqueous acid solution, preferably with an aqueous solution of a mineral acid. With respect to the ammonium salts which are preferably used, there is no general restriction, provided that the exchange of at least some of the counterions present in the one or more zeolites for ammonium can be accomplished. For example, it is possible for this purpose to use one or more ammonium salts selected from the group consisting of $NH_4NO_3$, $NH_4Cl$, $(NH_4)_2SO_4$ and mixtures of two or more thereof. The same applies correspondingly with respect to the acids and especially the mineral acids which can be used for the purpose of ion exchange, provided that the exchange of at least some of the counterions present in the one or more zeolites for $H^+$ can be accomplished. Thus, it is possible to use, for example, solutions of the mineral acids $HNO_3$, $HCl$, $H_2SO_4$, and also mixtures of two or more thereof for the ion exchange. With respect to the concentration of the solutions of protonated volatile bases or of acids used for the preferred ion exchange, there is no particular restriction whatsoever, provided that at least some of the counterions of the zeolite skeleton can be exchanged, and, in the case of use of one or more acids, that the pH of the solution does not lead to any significant dissolution of the zeolite skeleton. Thus, it is possible to use, for example, solutions of the salts or of the acids having a concentration of 1 to 50% by weight, preference being given to using concentrations of 5 to 30% by weight and more preferably of 10 to 25% by weight for the ion exchange. The same applies correspondingly with respect to the weight ratio of salt solution or acid solution to the one or more zeolites which are ion-exchanged. Thus, the weight ratio of the solution used for the ion exchange to the one or more zeolites may, for example, be in the range from 1 to 20, the weight ratio preferably being in the range from 2 to 10 and further preferably in the range from 4 to 7.

In particularly preferred embodiments, an ion exchange is thus performed prior to provision of the one or more zeolites in step (i). In the particularly preferred embodiments of the preparation of the catalyst used in the process according to the invention in which an ion exchange step with a protonated volatile base, and preferably with a protonated volatile amine, more preferably with ammonium, is performed, it is further preferred that, after the ion exchange and an optional wash step and/or after an optional drying step, a further calcining step is performed in order to remove the volatile base and more preferably ammonia completely from the ion-exchanged zeolite.

With regard to the manner of impregnation in step (ii) and in (ix) of the process according to the invention, the impregnation can be performed by any suitable process, for example an impregnation by soaking, spray impregnation and/or capillary impregnation. In particularly preferred embodiments of the process according to the invention, however, the impregnation in step (ii) is achieved by spray impregnation.

With regard to the solids concentration of the mixture provided in (v) or (v.3), according to the present invention, there are no particular restrictions whatsoever, provided that homogenizing of the mixture according to step (vi) and extrusion in (vii) of the homogenized mixture obtained in (vi) are possible. Thus, the solids concentration of the mixture provided in (v) or (v.3) may, for example, be in the range of 60-90% by weight, the solids concentration according to the present invention preferably being in the range of 65-85% by weight and further preferably in the range of 70-80% by weight. In particularly preferred embodiments of the process according to the invention for preparing a catalyst, the solids concentration of the mixture provided in (v) or (v.3) is in the range of 73-77% by weight.

With regard to the homogenizing in step (vi) too, according to the present invention, there is no particular restriction whatsoever, and so it is possible to select any conceivable procedure in order to obtain a homogeneous mixture of the mixture prepared in step (v) or (v.3), for which purpose it is possible to use, for example, one or more processes selected from the group consisting of stirring, kneading, agitating, vibration or a combination of two or more thereof. According to the present invention, the mixture prepared in step (v) or (v.3) is preferably homogenized by stirring and/or by kneading in step (vi), particular preference being given to homogenizing in step (vi) by kneading.

In particularly preferred embodiments of the process according to the invention for preparing a catalyst, in the preparation of the mixture in step (v), a first mixture comprising the one or more impregnated and optionally dried and/or calcined zeolites of the MFI, MEL and/or MWW structure type and the particles of the one or more metal oxides and/or precursor compounds of the one or more particles of the one or more metal oxides is first prepared, this preferably being treated with a peptizing aid prior to addition of the one or more solvents, the peptizing preferably being performed by means of an acid treatment. With regard to the acid used for the preferred acid treatment, according to the present invention, there is no particular restriction whatsoever with respect to the amount or type of the acid which is used for the acid treatment, this being selected in each case such that the components of the first mixture are merely etched and the one or more zeolites and the particles of the one or more metal oxides and/or precursor compounds are attacked only insignificantly thereby, more particularly such that the action thereof as a catalyst is not substantially restricted thereby. According to the present invention, preference is thus given to using weak acids and especially short-chain carboxylic acids for this purpose, preferably $(C_1-C_4)$-carboxylic acids, further preferably $(C_1-C_3)$-carboxylic acids, further preferably acetic and/or formic acid, and especially formic acid is used for the preferred acid treatment.

In the alternative of the process according to the invention in which the mixture obtained in (v.1) is admixed in (v.2) with one or more acids of phosphorus, it is, however, preferable that the peptizing is effected by means of this step. With regard to the acid or acids of phosphorus used for the acid treatment, there is no particular restriction according to the present invention with regard to the amount or type of the acid or acids of phosphorus which are used for the acid treatment, these preferably being selected such that the components of the first mixture are merely etched and the one or more zeolites and the particles of the one or more metal oxides and/or precursor compounds thereof are attacked only insignificantly thereby, more particularly such that the action thereof as a catalyst is not substantially restricted as a result. According to the present invention, it is thus possible in principle to use any suitable acid of phosphorus, and also any suitable mixture of two or more acids of phosphorus. In particular embodiments of the alternative of the process according to the invention, one or more acids of phosphorus selected from the group consisting of phosphinic acid, phosphonic acid, phosphoric acid, peroxophosphoric acid, hypodiphosphonic acid, diphosphonic acid, hypodiphosphoric acid, diphosphoric acid, peroxodiphosphoric acid and mixtures of two or more thereof are used in (v.2). Further preferably, one or more acids of phosphorus selected from the group consisting of phosphonic acid, phosphoric acid, diphosphonic acid, disphosphoric acid and mixtures of two or more thereof are used, further preferably from the group consisting of phosphoric acid, diphosphoric acid and mixtures thereof, and, in particularly preferred embodiments of the alternative of the process according to the invention in which the mixture obtained in (v.1) is admixed in (v.2) with one or more acids of phosphorus, phosphoric acid is used for this purpose.

In further preferred embodiments of the process according to the invention for preparing a catalyst, a viscosity additive and preferably a plasticizing aid is used for the preparation of the mixture in (v) or (v.3). With regard to the viscosity additives and especially the plasticizing aids which can be used in the preferred embodiments of the process according to the invention, there are no particular restrictions, provided that they are suitable for influencing the viscosity of the mixture in the desired manner, and especially in order to establish a viscosity of the mixture obtained in (v) or (v.3) and especially of the homogenized mixture obtained in (vi) suitable for the extrusion of the homogenized mixture in step (vii). Particular preference is given to using viscosity additives and especially the plasticizing aids according to the present invention which can be removed from the extrudate at least partly and preferably substantially without residue, especially by the optional drying step in (viii) and/or by the optional calcining step in step (ix), and preference is further given to using a plasticizing aid which volatilizes out of the extrudate in step (viii) and/or (ix) and/or decomposes as a result of thermolysis in step (viii) in the case of preferred heating of the extrudate and/or in step (ix) as a result of pyrolysis to give volatile compounds and especially to gases which can correspondingly escape from the extrudate. Thus, according to the preferred embodiments, it is possible in principle to use any suitable substance or any suitable substance mixtures as plasticizing aids, preference being given to using those which, according to the particular and preferred embodiments of the process according to the invention for preparing a catalyst, can be removed from the extrudate at least partly and preferably substantially without residue. The plasticizing aids used are thus preferably organic substances or substance mixtures and especially organic polymers, and further preferably starch derivatives.

With regard to the viscosity of the mixture obtained in (v) or (v.3) and especially of the homogenized mixture obtained in (vi), there are no particular restrictions in principle according to the present invention, provided that the viscosity is suitable for obtaining an extrudate in step (vii). Thus, the viscosity of the mixture obtained in (v) or (v.3) and especially of the homogenized mixture obtained in (vi) may be in the range from $0.1 \times 10^4$ to $4 \times 10^4$ N/m$^2$, the viscosity preferably being in the range from $0.5 \times 10^4$ to $3 \times 10^4$ N/m$^2$, further preferably from $1 \times 10^4$ to $2.5 \times 10^4$ N/m$^2$, further preferably from $1.3 \times 10^4$ to $2 \times 10^4$ N/m$^2$, further preferably from $1.5 \times 10^4$ to $1.8 \times 10^4$ N/m$^2$, further preferably from $1.55 \times 10^4$ to $1.7 \times 10^4$ N/m$^2$, further preferably from $1.6 \times 10^4$ to $1.65 \times 10^4$ N/m$^2$. According to the present invention, the viscosity preferably relates to the viscosity which is measured with a curdmeter, and more preferably a "Curdmeter MAX ME-500" (from Asuka Kiki).

With regard to the impregnation of the optionally dried and/or calcined extrudate in step (x) or the admixing of the mixture obtained in (v.1) in step (v.2) with a phosphorus-comprising solution, according to the present invention, there is no particular restriction whatsoever with respect to the phosphorus-comprising solution which can be used for this purpose, provided that the impregnation leads, after optional drying in step (xi) or (viii) and/or optional calcining in step (xii) or (ix), to an at least partly oxidic form of the phosphorus present in the particles of the one or more metal oxides. Thus, it is possible in principle to use any suitable phosphorus-comprising solution for this purpose. According to the present invention, it is possible to use, for example, phosphorus- and oxygen-containing salts and/or acids, the solubility being based especially on the particular and preferred solvents according to the present invention which are used especially in step (x) or (v.2) of the process according to the invention. Thus, it is possible to use solutions of phosphinates, phosphonates, phosphates, peroxophosphates, hypodiphosphonates, diphosphonates, hypodiphosphates, diphosphates, peroxodiphosphates and mixtures of two or more thereof, in each case as salts and/or acids.

According to the present invention, however, it is preferable to use a solution and especially an aqueous solution of a phosphorus- and oxygen-comprising salt and/or acid which derive(s) from the salts selected from the group of the phosphonates, phosphates, diphosphonates, diphosphates and mixtures of two or more thereof, and especially a phosphorus-comprising solution is used in step (x) or (v.2) which comprises one or more acids of phosphorus, preferably selected from the group consisting of phosphonic acid, phosphoric acid, diphosphonic acid, diphosphoric acid and mixtures of two or more thereof, preferably as an aqueous solution. Particular preference is given to using phosphoric acid solutions for impregnation of the optionally dried and/or calcined extrudate in step (x) or for the admixing of the mixture obtained in (v.1) in step (v.2) of the process according to the invention, preferably aqueous phosphoric acid solutions.

With regard to the phosphorus-comprising solutions, especially according to the particular and preferred embodiments of the present invention, there is no restriction whatsoever in principle with respect to the concentration of phosphorus present therein, provided that suitable impregnation of the optionally dried and/or calcined extrudate can be achieved in step (x) or that it is suitable for admixing the mixture obtained in (v.1) in step (v.2). In the preferred embodiments of the present invention in which phosphorus- and oxygen-containing salts and/or acids are used, it is thus possible, for example, to use total concentrations of the phosphorus- and oxygen-containing salts and/or acids in the solutions in the range from 0.1 to 90% by weight of the solution used and preferably of the aqueous solutions used. According to the present invention, however, preference is given to using concentrations of the phosphorus- and oxygen-containing salts and/or acids according to the particular and preferred embodiments of the invention in the range from 0.5 to 70% by weight, further preferably from 1 to 50% by weight, further preferably from 5 to 40% by weight, further preferably from 10 to 35% by weight, further preferably from 15 to 30% by weight and even further preferably from 18 to 25% by weight. In particularly preferred embodiments of the process according to the invention, the concentration of the preferred phosphorus- and oxygen-containing salts and/or acids in step (x) of the process according to the invention is in the range from 19 to 22% by weight based on the total weight of the solution used. In the alternative of the process according to the invention in which the mixture obtained in (v.1) is admixed in (v.2) with a phosphorus-comprising solution, preferably with one or more acids of phosphorus and further preferably with phosphoric acid, preference is given to using total concentrations of the phosphorus- and oxygen-containing salts and/or acids in the solutions in the range from 5 to 99% by weight of the solution used and preferably of the aqueous solutions used. According to the present invention, however, preference is given to using concentrations of the phosphorus- and oxygen-containing salts and/or acids as per the particular and preferred embodiments of the invention in the range from 10 to 98% by weight, further preferably from 30 to 95% by weight, further preferably from 50 to 92% by weight, further preferably from 60 to 90% by weight, further preferably from 70 to 89% by weight and even further preferably from 80 to 88% by weight. In particularly preferred embodiments of the process according to the invention, the concentration of the preferred phosphorus- and oxygen-containing salts and/or acids in step (x) of the process according to the invention is in the range from 83 to 87% by weight based on the total weight of the solution used.

In particular embodiments of the alternative of the process according to the invention in which the mixture obtained in (v.1) is admixed in (v.2) with a phosphorus-comprising solution, the optionally dried and/or calcined extrudate which is obtained correspondingly in (vii), (viii) and/or (ix) is then impregnated in a subsequent step (x) with a phosphorus-comprising solution in the process according to the invention or the particular and preferred embodiments thereof. In accordance with the process according to the invention, in these embodiments of the alternative of the process according to the invention, the impregnated extrudate obtained in (x) is optionally dried in a further step (xi) in the process according to the invention or the particular and preferred embodiments thereof, and optionally calcined in a further step (xii) in the process according to the invention or the particular and preferred embodiments thereof. Accordingly, the preparation in the embodiments mentioned includes a double introduction of the phosphorus into the one or more metal oxides and/or precursor compounds thereof in (v.2) and in (x). However, particular preference is given to embodiments of the alternative of the process according to the invention for preparing the inventive catalyst in which no impregnation of the extrudate obtained in (vii), (viii) and/or (ix) with phosphorus or a phosphorus-containing compound is effected. Thus, a particularly efficient process for preparing the inventive catalyst is provided.

In the process according to the invention for preparing the inventive catalyst, especially in the particular and preferred embodiments described in the present application, there is in principle no restriction whatsoever with regard to the properties and especially the particle sizes and/or morphologies of the one or more zeolites of the MFI, MEL and/or MWW structure type provided in step (i). According to the particle size of the zeolites provided in step (i), however, one or more steps are optionally performed during the process according to the invention, preferably after the impregnation in step (ii) or after the optional drying in step (iii) or after the optional calcining in step (iv), in order to bring the one or more zeolites to a preferred particle size. In this connection, there is at first no particular restriction with regard to the particle size of the one or more zeolites, provided that this is suitable for the performance of the further steps in the process according to the invention, especially according to the particular and preferred embodiments of the present invention, and the particle size should especially be suitable for performance of the extrusion in step (vii), more particularly depending on the size and/or shape of the extruded body. Thus, in particular embodiments of the process according to the invention, one or more steps are performed after the impregnation in step (ii) or after the optional drying in step (iii) or after the optional calcining in step (iv), in order to bring the one or more impregnated and optionally dried and/or calcined zeolites of the MFI, MEL and/or MWW structure type to a particle size $D_{50}$ in the range from 5 to 1000 μm. In further preferred embodiments of the process according to the invention, the one or more zeolites are brought after one or more of the aforementioned steps, in one or more steps, to a particle size $D_{50}$ in the range from 10 to 750 µm, further preferably from 30 to 500 µm, further preferably from 50 to 300 µm, further preferably from 70 to 200 µm and even further preferably from 80 to 150 µm. In yet further preferred embodiments of the process according to the invention, the one or more impregnated and optionally dried and/or calcined zeolites, after the impregnation in step (ii) or after the drying in step (iii) or after the calcining in step (iv), is brought in one or more steps to a particle size $D_{50}$ in the range from 90 to 120 µm. With regard to the number of steps and the manner in which the one or more zeolites are brought to a particular or preferred particle size $D_{50}$, according to the present invention, there are no restrictions whatsoever, and so it is possible in principle to use any suitable process for this purpose. According to the present invention, however, the one or more zeolites are preferably subjected to one or more grinding steps after one or more of steps (ii) and optional steps (iii) and (iv).

Thus, according to the present invention, preference is given to embodiments of the process for preparing a catalyst according to the present invention, and especially a catalyst according to one of the particular or preferred embodiments thereof, in which the impregnating in (ii) or the drying in (iii) or the calcining in (iv) is followed by bringing of the one or more impregnated zeolites of the MFI, MEL and/or MWW structure type to a particle size $D_{50}$ in the range from 5 to 1000 µm, further preferably from 10 to 750 µm, further preferably from 30 to 500 µm, further preferably from 50 to 300 µm, further preferably from 70 to 200 µm, further preferably from 80 to 150 µm, even further preferably from 90 to 120 µm, preferably by grinding.

According to the present invention, in the process according to the invention, a drying step is performed according to one or more of steps (iii), (viii) and/or (xi). With regard to the manner in which the optional drying is achieved in one or more of these steps, there is no restriction whatsoever in principle, and so the drying can be performed at any suitable temperature and in any suitable atmosphere. Thus, the optional drying can be effected under a protective gas atmosphere or in air, the optional drying preferably being effected in air. With regard to the temperature at which the drying is effected, it is possible, for example, to select a temperature in the range from 50 to 220° C. According to the present invention, the optional drying according to one or more of steps (iii), (viii) and/or (xi) is effected at a temperature in the range from 70 to 180° C., further preferably from 80 to 150° C., further preferably from 90 to 130° C. and further preferably in the range from 100 to 125° C. In particularly preferred embodiments of the process according to the invention, the drying according to one or more of steps (iii), (viii) and/or (xi) is effected at a temperature in the range from 110 to 120° C. With regard to the duration of the one or more optional drying steps, especially in particular and preferred embodiments of the process according to the invention, there is no particular restriction, provided that drying suitable for the further process steps can be achieved, for example after a drying step having a duration of 1 to 50 hours. In particular embodiments of the process according to the invention, the optional drying is performed for a period of 5 to 40 h, further preferably of 8 to 30 h, further preferably of 10 to 25 h, further preferably of 12 to 20 h and still further preferably of 14 to 18 h.

Thus, according to the present invention, preference is given to embodiments of the process for preparing a catalyst according to the present invention, and especially a catalyst according to one of the particular or preferred embodiments thereof, in which the drying in (iii), (viii) and/or (xi) is effected at a temperature in the range from 50 to 220° C., preferably from 70 to 180° C., further preferably from 80 to 150° C., further preferably from 90 to 130° C., further preferably from 100 to 125° C., and further preferably from 110 to 120° C.

With regard to the optional calcining steps according to the present invention, the same applies in principle as with regard to the optional drying steps, and so no particular restriction whatsoever exists here either, either with regard to the temperature or with regard to the atmosphere in which the calcination is performed, and finally also not with regard to the duration of a calcination according to the particular and preferred embodiments of the present invention, provided that the product of the calcination is an intermediate suitable for being processed in the further steps of the process according to the invention to give a catalyst according to the present invention. Thus, for example, with regard to the temperature of the optional calcining in one or more of the optional steps (iv), (ix) and/or (xii), a temperature in the range from 300 to 850° C. may be selected, preference being given to selecting a temperature in the range from 350 to 750° C., further preferably from 400 to 700° C., further preferably from 450 to 650° C. and even further preferably from 480 to 600° C. In yet further preferred embodiments of the present invention, the calcination in one or more of the optional steps (iv), (ix) and/or (xii) is performed at a temperature of 500 to 550° C. With regard to the atmosphere in which the optional calcination according to one or more of the aforementioned steps of the process according to the invention is performed, this may be either an inert atmosphere or air, the optional calcination in one or more of the optional steps (iv), (ix) and/or (xii) preferably being performed in air. Finally, there is also no restriction whatsoever with regard to the duration of the calcination step in the optional steps (iv), (ix) and/or (xii), provided that the product of the calcination is suitable for further use, especially as an intermediate according to the optional steps (iv) and/or (ix), in the process according to the invention for preparing a catalyst, especially a catalyst according to one of the particular or preferred embodiments of the present application. Thus, the duration of the calcination according to one or more of the optional calcination steps in (iv), (ix) and/or (xii) may, for example, be 0.5 to 20 hours, preference being given to a duration of 1 to 15 h, further preferably of 2 to 10 h, further preferably of 3 to 7 h, and particular preference to a duration of 4 to 5 h.

Thus, according to the present invention, preference is given to embodiments of the process for preparing a catalyst according to the present invention, and especially a catalyst according to one of the particular or preferred embodiments thereof, in which the calcining in (iv), (ix) and/or (xii) is effected at a temperature in the range from 300 to 850° C., preferably from 350 to 750° C., further preferably from 400 to 700° C., further preferably from 450 to 650° C., further preferably from 480 to 600° C., and further preferably from 500 to 550° C.

In steps (ii) and (x) of the process according to the invention, the one or more zeolites of the MFI, MEL and/or MWW structure type are first impregnated with a solution comprising one or more alkaline earth metals, or the optionally dried and/or calcined extrudate is impregnated with a phosphorus-comprising solution. According to the present invention, there is no restriction whatsoever either with respect to step (ii) or with respect to step (x) with regard to the type and/or number of solvents used for this purpose. Thus, it is possible in principle to use any suitable solvent or solvent mixture in steps (ii) and (x), provided that it is suitable for bringing about a corresponding impregnation of the materials defined therein, especially according to the particular and preferred embodiments of the present invention. This is equally true of the one or more solvents which are used in step (v) or (v.3) for preparation of the mixture defined therein, provided that the one or more solvents used for this purpose are suitable for enabling homogenization in step (vi) and the extrusion in step (vii). For example, it is possible in one or more of steps (ii), (x) and/or (v) or (v.3) to use one or more solvents selected from the group consisting of alcohols, water, mixtures of two or more alcohols and mixtures of water and one or more alcohols. In preferred embodiments of the present invention, the one or more solvents used in (ii), (x) and/or (v) or (v.3) are selected from the group consisting of ($C_1$-$C_6$)-alcohols, water, mixtures of two or more ($C_1$-$C_6$)-alcohols and mixtures of water and one or more ($C_1$-$C_6$)-alcohols, the one or more solvents further preferably being from the group consisting of ($C_1$-$C_4$)-alcohols, water, mixtures of two or more ($C_1$-$C_4$)-alcohols and mixtures of water and one or more ($C_1$-$C_4$)-alcohols. In further preferred embodiments, the one or more solvents in steps (ii), (x) and/or (v) or (v.3) are selected from the group consisting of methanol, ethanol, n-propanol, isopropanol, water and mixtures of two or more thereof, further preferably from the group consisting of methanol, ethanol, water and mixtures of two or more thereof, the solvent even further preferably being water, preferably distilled water.

Thus, according to the present invention, preference is given to embodiments of the process for preparing a catalyst according to the present invention, and especially a catalyst according to one of the particular or preferred embodiments thereof, in which the solution used in (ii) and/or (x) or (v.2) and/or the mixture prepared in (v) or (v.3) comprises one or more solvents selected from the group consisting of alcohols, water, mixtures of two or more alcohols, and mixtures of water and one or more alcohols, preferably from the group consisting of ($C_1$-$C_6$) alcohols, water, mixtures of two or more ($C_1$-$C_6$) alcohols, and mixtures of water and one or more ($C_1$-$C_6$) alcohols, further preferably ($C_1$-$C_4$) alcohols, water, mixtures of two or more ($C_1$-$C_4$) alcohols, and mixtures of water and one or more ($C_1$-$C_4$) alcohols, further preferably consisting of methanol, ethanol, n-propanol, isopropanol, water and mixtures of two or more thereof, further preferably consisting of methanol, ethanol, water and mixtures of two or more thereof, the solvent further preferably being water, preferably distilled water.

As well as a catalyst for the conversion of oxygenates to olefins according to the present invention as described in the present application, and especially according to the particular and preferred embodiments thereof, the present invention likewise relates to those catalysts for the conversion of oxygenates to olefins which are obtainable by the preparation process according to the invention, i.e. including catalysts per se which can, for example, be obtained by the preparation process according to the invention, without necessarily having to be prepared by this process. More particularly, the present invention thus relates to catalysts for the conversion of oxygenates to olefins which can be prepared by the process according to the invention, especially according to the particular and preferred embodiments thereof described in the present application, but can be or have been prepared by another process suitable for this purpose.

Thus, according to the present invention, preference is given to embodiments of the catalyst for the conversion of oxygenates to olefins in which the catalyst, and especially the catalyst according to one of the particular or preferred embodiments of the present invention, is obtainable by the process according to the invention for preparing a catalyst, preferably by one of the particular or preferred embodiments of the process according to the invention.

As well as a catalyst for the conversion of oxygenates to olefins and a process for preparing such a catalyst, the present invention also relates to a process for converting oxygenates to olefins. More particularly, the present invention relates to such a process comprising:

(1) providing a gas stream comprising one or more oxygenates;

(2) contacting the gas stream with a catalyst according to the present invention.

With regard to the catalyst which can be used in the process according to the invention for converting oxygenates to olefins, there is in principle no restriction whatsoever, provided that it is a catalyst according to the present invention as obtainable, for example, also by the process according to the invention, and provided that this catalyst is suitable for the conversion of at least one oxygenate to at least one olefin. This is especially true of the embodiments of the inventive catalyst according to the particular and preferred embodiments of the present invention.

The same applies correspondingly to the one or more oxygenate(s) present in the gas stream according to (1), and so there is no restriction here whatsoever in principle in the process according to the invention, provided that the one or more oxygenates present in the gas stream according to (1) can be converted by one of the catalysts according to the present invention and especially according to the particular and preferred embodiments thereof to at least one olefin when contacted according to (2). According to the present invention, however, it is preferable that the one or more oxygenates present in the gas stream according to (1) are selected from the group consisting of aliphatic alcohols, ethers, carbonyl compounds and mixtures of two or more thereof. Further preferably, the one or more oxygenates are selected from the group consisting of ($C_1$-$C_6$)-alcohols, di($C_1$-$C_3$)alkyl ethers, ($C_1$-$C_6$)-aldehydes, ($C_2$-$C_6$)-ketones and mixtures of two or more thereof, further preferably consisting of ($C_1$-$C_4$)-alcohols, di($C_1$-$C_2$)alkyl ethers, ($C_1$-$C_4$)-aldehydes, ($C_2$-$C_4$)-ketones and mixtures of two or more thereof. In yet further preferred embodiments of the present invention, the gas stream according to (1) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, the one or more oxygenates further preferably being selected from the group consisting of methanol, ethanol, dimethyl ether, diethyl ether, ethyl methyl ether and mixtures of two or more thereof. In particularly preferred embodiments of the process according to the invention for converting oxygenates to olefins, the gas stream according to (1) comprises methanol and/or dimethyl ether as the one or more oxygenates, and dimethyl ether is more preferably the oxygenate present in the gas stream according to (1).

Thus, according to the present invention, preference is given to embodiments of the process for converting oxygenates to olefins in which the gas stream according to (1) comprises one or more oxygenates selected from the group consisting of aliphatic alcohols, ethers, carbonyl compounds and mixtures of two or more thereof, preferably consisting of ($C_1$-$C_6$) alcohols, di($C_1$-$C_3$)alkyl ethers, ($C_1$-$C_6$) aldehydes, ($C_2$-$C_6$) ketones and mixtures of two or more thereof, further preferably consisting of ($C_1$-$C_4$) alcohols, di($C_1$-$C_2$)

alkyl ethers, ($C_1$-$C_4$) aldehydes, ($C_2$-$C_4$) ketones and mixtures of two or more thereof, further preferably from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, further preferably from the group consisting of methanol, ethanol, dimethyl ether, diethyl ether, ethyl methyl ether and mixtures of two or more thereof, the gas stream further preferably comprising methanol and/or dimethyl ether, and more preferably dimethyl ether.

On the other hand, with regard to the content of oxygenates in the gas stream according to (1) to the process according to the invention for converting oxygenates to olefins, there is no restriction whatsoever according to the present invention here either, provided that, when the gas stream is contacted in (2) with a catalyst according to the present invention, at least one oxygenate can be converted to at least one olefin. In preferred embodiments, the content of oxygenates in the gas stream according to (1) is in the range from 30 to 100% by volume based on the total volume, the content especially being based on a gas stream at a temperature in the range from 200 to 700° C. and at a pressure of 101.3 kPa, preferably at a temperature in the range from 250 to 650° C., further preferably from of 300 to 600° C., further preferably from 350 to 560° C., further preferably from 400 to 540° C., further preferably from 430 to 520° C., and further preferably in the range from 450 to 500° C. and at a pressure of 101.3 kPa. According to the present invention, it is further preferred that the content of oxygenates in the gas stream according to (1) is in the range from 30 to 99% by volume, further preferably from 30 to 95% by volume, further preferably from 30 to 90% by volume, further preferably from 30 to 80% by volume, further preferably from 30 to 70% by volume, further preferably from 30 to 60% by volume and further preferably from 30 to 50% by volume. In particularly preferred embodiments of the process according to the invention for converting oxygenates to olefins, the content of oxygenates in the gas stream according to (1) is in the range from 30 to 45% by volume.

Thus, according to the present invention, preference is given to embodiments of the process for converting oxygenates to olefins in which the content of oxygenates in the gas stream according to (1) is in the range from 30 to 100% by volume based on the total volume, preferably from 30 to 99% by volume, further preferably from 30 to 95% by volume, further preferably from 30 to 90% by volume, further preferably from 30 to 80% by volume, further preferably from 30 to 70% by volume, further preferably from 30 to 60% by volume, further preferably from 30 to 50% by volume, and further preferably from 30 to 45% by volume.

With regard to the other components in the gas stream according to (1) in the process according to the invention, there is in principle no restriction whatsoever, provided that the gas stream is suitable overall for converting at least one of the oxygenates to at least one olefin in step (2) when contacted with a catalyst according to the present invention. In addition, for example, as well as the one or more oxygenates in the gas stream according to (1), one or more inert gases may also be present therein, for example one or more noble gases, nitrogen, carbon monoxide, carbon dioxide, water and mixtures of two or more thereof. In particular embodiments of the present invention, the gas stream according to (1) of the process according to the invention, as well as the one or more oxygenates, comprises water.

With regard to those preferred embodiments in which, as well as the one or more oxygenates, water is present in the gas stream according to (1), there is no restriction in principle with respect to the water content which may be present therein, provided that the conversion of at least one oxygenate in the gas stream to at least one olefin in step (2) of the contacting of the gas stream can be effected with a catalyst according to the present invention. In these preferred embodiments, however, it is preferable that the water content in the gas stream is in the range from 5 to 60% by volume based on the total volume, the water content more preferably being in the range from 10 to 55% by volume, further preferably from 20 to 50% by volume and further preferably from 30 to 45% by volume.

Thus, according to the present invention, preference is given to embodiments of the process for converting oxygenates to olefins in which water is present in the gas stream according to (1), preferably in the range from 5 to 60% by volume based on the total volume, preferably from 10 to 55% by volume, further preferably from 20 to 50% by volume, and further preferably from 30 to 45% by volume.

In particularly preferred embodiments of the process according to the invention for converting oxygenates to olefins, the gas stream provided in (1) originates from a preliminary reaction, preferably from the conversion of one or more alcohols to one or more ethers, especially from the conversion of one or more alcohols selected from the group consisting of methanol, ethanol, n-propanol, isopropanol and mixtures of two or more thereof, further preferably from the group consisting of methanol, ethanol, n-propanol and mixtures of two or more thereof, the gas stream provided in (1) more preferably originating from a preliminary reaction of methanol and/or ethanol and methanol further preferably being at least partly converted to one or more di($C_1$-$C_2$)alkyl ethers, preferably to one or more di($C_1$-$C_2$)alkyl ethers selected from the group consisting of dimethyl ether, diethyl ether, ethyl methyl ether and mixtures of two or more thereof. For instance, the gas stream provided in (1), in a particularly preferred embodiment, originates from a preliminary reaction of conversion of methanol to dimethyl ether.

In the particularly preferred embodiments of the process according to the invention in which the gas stream provided in (1) originates from a preliminary reaction of one or more alcohols, there is no particular restriction whatsoever in principle with respect to the reaction and hence the reaction product of the conversion of one or more alcohols, provided that this leads to a gas stream comprising one or more oxygenates which, when contacted in (2) with a catalyst according to the present invention, enables the conversion of at least one of the oxygenates to at least one olefin. In these particular embodiments, it is further preferable that the preliminary reaction leads to conversion of at least one alcohol to at least one ether and especially to at least one dialkyl ether, the preliminary reaction more preferably being a dehydration in which water is obtained as a coproduct to one or more dialkyl ethers. In the particular and preferred embodiments of the present invention in which the gas stream provided in (1) originates from a preliminary reaction, it is particularly preferred in the process according to the invention that such a gas stream originating from a preliminary reaction is supplied directly and without workup to the process according to the invention in step (1).

With respect to the manner of contacting the gas stream with a catalyst according to the present invention in step (2) of the process according to the invention for converting oxygenates to olefins, there is in principle no restriction whatsoever, provided that the conversion of at least one oxygenate to at least one olefin can be implemented. This applies, for example, to the temperature at which the contacting (2) takes place. Thus, for example, the contacting in step (2) of the process according to the invention can take place at a temperature in the range from 200 to 700° C., preference being given to selecting temperatures in the range from 250 to 650° C., further preferably from 300 to 600° C., further preferably from 350 to 560° C., further preferably from 400 to 540° C. and further preferably from 430 to 520° C. In particularly preferred embodiments of the present invention, the contacting according to (2) of the process according to the invention is performed at a temperature in the range from 450 to 500° C.

Thus, according to the present invention, preference is given to embodiments of the process for converting oxygenates to olefins in which the contacting according to (2) is effected at a temperature in the range from 200 to 700° C., preferably from 250 to 650° C., further preferably from 300 to 600° C., further preferably from 350 to 560° C., further preferably from 400 to 540° C., further preferably from 430 to 520° C., and further preferably from 450 to 500° C.

The same applies correspondingly to the pressure at which the gas stream is contacted in step (2) of the process according to the invention with the catalyst according to the present invention. Thus, the contacting can in principle take place at any desired pressure, provided that this allows the conversion of at least one oxygenate to at least one olefin by virtue of the contacting of the gas stream with the catalyst. Thus, the pressure, for example in the contacting in step (2), may be in the range from 0.1 to 10 bar, the pressure according to the present application indicating the absolute pressure, such that a pressure of 1 bar in the contacting accordingly corresponds to the standard pressure of 1.03 kPa. According to the present invention, the contacting in step (2) takes place preferably at a pressure from 0.3 to 7 bar, further preferably from 0.5 to 5 bar, further preferably from 0.7 to 3 bar, further preferably from 0.8 to 2.5 bar and further preferably from 0.9 to 2.2 bar. In particularly preferred embodiments of the process according to the invention for converting oxygenates to olefins, the contacting in step (2) takes place at a pressure of 1 to 2 bar.

Thus, according to the present invention, preference is given to embodiments of the process for converting oxygenates to olefins in which the contacting according to (2) is effected at a pressure in the range from 0.1 to 10 bar, preferably from 0.3 to 7 bar, further preferably from 0.5 to 5 bar, further preferably from 0.7 to 3 bar, further preferably from 0.8 to 2.5 bar, further preferably from 0.9 to 2.2 bar, and further preferably from 1 to 2 bar.

In addition, there are no particular restrictions with respect to the manner of performance of the process according to the invention for converting oxygenates to olefins, and so it is possible to use either a continuous or a noncontinuous process, the noncontinuous process being performable, for example, in the form of a batch process. According to the present invention, however, it is preferable to conduct the process according to the invention for the conversion of oxygenates as a continuous process. Thus, according to the present invention, preference is given to embodiments of the process for converting oxygenates to olefins in which the process is a continuous process.

With respect to these preferred embodiments of a continuous process, there are no restrictions whatsoever with respect to the space velocity selected, provided that the conversion of an oxygenate to an olefin can be effected. Thus, it is possible to select, for example, space velocities (WHSV=weight hourly space velocity is calculated as the ratio of oxygenate reactant stream in kg/h to the amount of zeolite in the reactor in kg) in the contacting in step (2) which are in the range from 0.5 to 50 $h^{-1}$, preference being given to selecting space velocities from 1 to 30 $h^{-1}$, further preferably from 2 to 20 $h^{-1}$, further preferably from 3 to 15 $h^{-1}$ and further preferably from 4 to 10 $h^{-1}$. In particularly preferred embodiments of the process according to the invention for converting oxygenates, space velocities for the contacting of the gas stream in step (2) in the range from 5 to 7 $h^{-1}$ are selected.

With respect to the preferred space velocities according to the particular embodiments of the process according to the invention for converting oxygenates to olefins, these are preferably established in connection with a conversion of oxygenates within a particular range. Thus, the space velocities according to the particular and preferred embodiments of the process according to the invention may be established at a conversion of oxygenate in the range from, for example, 50 to 99.9%. According to the present invention, the space velocity according to the particular and preferred embodiments, however, is preferably established at a conversion of oxygenates in the range from 70 to 99.5%, further preferably from 90 to 99%, further preferably from 95 to 98.5%, further preferably from 96 to 98% and further preferably 96.5 to 97.5%. According to the present invention, however, it is further preferred that the space velocity in the course of contacting of the gas stream in step (2) of the process according to the invention is established at a full conversion from 96.5 to 99.9% or more of the oxygenate, further preferably from 97.5 to 99.9% or more, further preferably from 98 to 99.9% or more, further preferably from 99 to 99.9% or more and further preferably from 99.5 to 99.9% or more conversion of oxygenates.

Thus, according to the present invention, preference is given to embodiments of the process for converting oxygenates to olefins in which the space velocity in the course of contacting according to (2) is in the range from 0.5 to 50 $h^{-1}$, preferably from 1 to 30 $h^{-1}$, further preferably from 2 to 20 $h^{-1}$, further preferably from 3 to 15 $h^{-1}$, further preferably from 4 to 10 $h^{-1}$ and further preferably from 5 to 7 $h^{-1}$.

As described above and shown in the examples of the present application, it is possible to achieve particularly long service lives with the inventive catalyst in a process for converting oxygenates as described in the present application, especially with respect to the particular and preferred embodiments of the process according to the invention. It has thus been found that, surprisingly, the use of a catalyst according to the present invention can considerably increase the service life of the catalyst before the process has to be interrupted for regeneration of the catalyst, at least with respect to the use of this catalyst batch compared to the use of catalysts according to the prior art. It is thus particularly preferable according to the present invention to select long service lives for the performance of the process for converting oxygenates to olefins at one of the particular or preferred space velocities, as described in the present application.

Thus, preference is given to service lives in the range from 40 to 300 h, further preferably in the range from 50 to 250 h, further preferably from 70 to 200 h, further preferably from 90 to 150 h, further preferably from 100 to 130 h and further preferably from 110 to 115 h. More particularly, based on the particular and preferred space velocities at which the process according to the invention is performed, preference is thus given, for example, to service lives of 40 to 300 h at a space velocity in the range from 0.5 to 50 $h^{-1}$.

Further preference is given to a service life of 50 to 250 h at a space velocity in the range from 1 to 30 h$^{-1}$, further preference to a service life of 70 to 200 h at a space velocity in the range from 2 to 20 h$^{-1}$, further preference to a service life of 90 to 150 h at a space velocity in the range from 3 to 15 h$^{-1}$, and further preference to a service life of 100 to 130 h at a space velocity in the range from 4 to 10 h$^{-1}$. In a particularly preferred embodiment of the process according to the invention, a service life of the catalyst, during which the continuous process is performed without interruption, in the range from 110 to 115 h at a space velocity of 5 to 7 h$^{-1}$ is selected. As already above with respect to the particular and preferred space velocities which are selected in the process according to the invention, the particular and preferred embodiments with respect to the selected service life and especially the selected service lives in combination with particular space velocities relate to a simultaneous full conversion of the catalyst and especially to conversions in the range from 96.5 to 99.9% or more, preferably from 97.5 to 99.9% or more, further preferably from 98 to 99.9% or more, further preferably from 99 to 99.9% or more and further preferably from 99.5 to 99.9% or more with respect to the conversion of the one or more oxygenates present in the gas stream according to (1) of the process according to the invention.

Thus, according to the present invention, further preference is given to embodiments of the process for converting oxygenates to olefins in which the service life of the catalyst during which the continuous process is performed without interruption is in the range from 40 to 300 h, preferably from 50 to 250 h, further preferably from 70 to 200 h, further preferably from 90 to 150 h, further preferably from 100 to 130 h, and further preferably from 110 to 115 h.

The present invention further also relates to the use of the inventive catalyst as described above, and especially to the use of the inventive catalyst according to the particular and preferred embodiments as described in the present application. According to the present invention, there is no restriction whatsoever in principle with respect to the use of the inventive catalyst, and so it can be used either for the conversion of oxygenates to olefins or in any conceivable catalytic process in which the catalyst exhibits a corresponding catalytic action with respect to a chemical conversion. According to the present invention, however, the inventive catalyst is preferably used in a methanol-to-olefin process (MTO process), and further preferably in a methanol-to-gasoline process (MTG process), in a methanol-to-hydrocarbon process, in a methanol-to-propylene process (MTP process), in a methanol-to-propylene/butylene process (MT3/4 process) and for alkylation of aromatics, or in a fluid catalytic cracking process (FCC process). According to the present invention, however, the inventive catalyst is more preferably used in a methanol-to-olefin process (MTO process), especially in a process for converting oxygenates to olefins in one of the particular or preferred processes for converting oxygenates to olefins according to the present invention.

DESCRIPTION OF THE FIGURES

FIG. 1 shows the methanol conversion and the respective ethylene, propylene, $C_4$ olefin, $C_4$ paraffin and methane selectivities of the catalyst according to example 1 in the MTO test according to example 3 as a function of run time. The abscissa axis represents the service life in hours, the left-hand ordinate axis the selectivity in % for ethylene (measurement points: "♦"), propylene (measurement points: "▲"), $C_4$ olefin (measurement points: "□"), aromatics (measurement points: "●"), and methane (measurement points: "■"), and the right-hand ordinate axis the methanol or dimethyl ether conversion in % which is shown in the graph as a continuous line.

Figure 2:
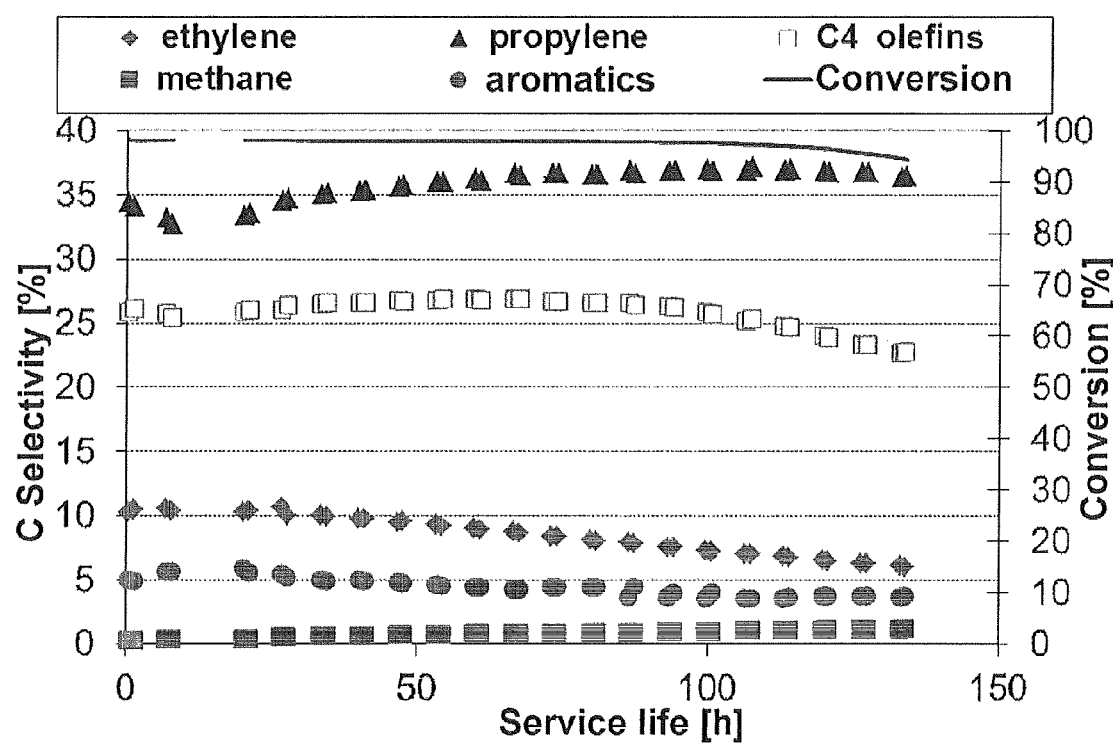
FIG. 2 shows the methanol conversion and the respective ethylene, propylene, C4 olefin, C4 paraffin and methane selectivities of the catalyst according to example 1 in the MTO test according to example 3 as a function of run time. The abscissa axis represents the service life in hours, the left-hand ordinate axis the selectivities in % for ethylene (measurement points: "♦"), propylene (measurement points: "▲"), C4 olefin (measurement points: "□"), aromatics (measurement points: "●"), and methane (measurement points: "■"), and the right-hand ordinate axis the methanol or dimethyl ether conversion in % which is shown in the graph as a continuous line.

FIG. 2 shows the methanol conversion and the respective ethylene, propylene, $C_4$ olefin, $C_4$ paraffin and methane selectivities of the catalyst according to example 1 in the MTO test according to example 3 as a function of run time. The abscissa axis represents the service life in hours, the left-hand ordinate axis the selectivities in % for ethylene (measurement points: "♦"), propylene (measurement points: "▲"), $C_4$ olefin (measurement points: "□"), aromatics (measurement points: "●"), and methane (measurement points: "■"), and the right-hand ordinate axis the methanol or dimethyl ether conversion in % which is shown in the graph as a continuous line.

Figure 3:
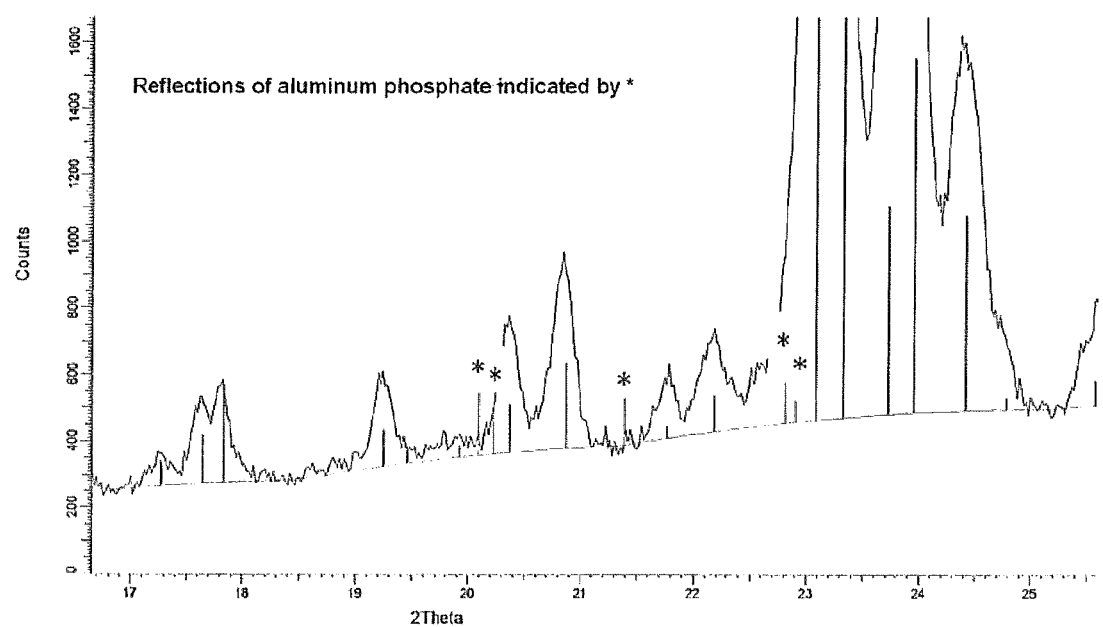
FIG. 3 shows a section from the x-ray diffractogram of the extrudate from example 1 which was measured with a wavelength of 1.54060 Å. The abscissa axis represents the reflection angle "2theta" in °2theta, and the ordinate axis the measured intensity in the dimensionless unit "counts". For comparative purposes, the line spectra of ZSM-5 and of aluminum phosphate (AlPO4) have been included in the diffractogram, the lines for aluminum phosphate being marked with a "*". More particularly, it can be inferred from the x-ray diffractogram that no AlPO4 is present in the sample.

FIG. 3 shows a section from the x-ray diffractogram of the extrudate from example 1 which was measured with a wavelength of 1.54060 Å. The abscissa axis represents the reflection angle "2theta" in °2theta, and the ordinate axis the measured intensity in the dimensionless unit "counts". For comparative purposes, the line spectra of ZSM-5 and of aluminum phosphate ($AlPO_4$) have been included in the diffractogram, the lines for aluminum phosphate being marked with a "*". More particularly, it can be inferred from the x-ray diffractogram that no $AlPO_4$ is present in the sample.

EXAMPLES

Comparative Example 1

Preparation of an Extrudate Comprising ZSM-5

150 g of H-ZSM-5 (ZEO-cat PZ2-100 H from Zeochem) with Si/Al=50 were mixed with 130 g of pseudoboehmite (Pural SB; Sasol), admixed with 3.9 g of formic acid and processed with 135 g of water in a kneader to give a homogeneous material. The starting weights were selected such that the zeolite/binder ratio in the calcined extrudates corresponds to 60:40. This kneaded material was pushed with the aid of an extrudate press at approx. 90-130 bar through a 2.5 mm die. The extrudates were subsequently dried in a drying cabinet at 120° C. for 16 h and (after heating time 4 h) calcined in a muffle furnace at 500° C. for 4 h. Thereafter, the extrudates were processed in a sieving machine with 2 steel balls (diameter approx, 2 cm, 258 g/ball) to give 1.6-2.0 mm spall.

The BET surface area of the resulting spall was 351 m$^2$/g.
Elemental analysis:
Si: 25.9 g/100 g
Al: 19.7 g/100 g Comparative Example 2

Preparation of a Phosphorus-Treated Extrudate Comprising ZSM-5

Prior to the phosphorus impregnation, the water absorption capacity of the H-ZSM-5/Al$_2$O$_3$ spall from comparative example 1 was determined to be 1 ml H$_2$O/2 g of extrudate.

Accordingly, a solution of 3.1 g of 85% phosphoric acid was made up to total liquid 10 ml with dist. water. The amount of phosphoric acid was calculated such that, after the calcination, 4% by weight of phosphorus, calculated as the element, is present on the extrudate. 20 g of spall from comparative example 1 were placed in a porcelain dish and homogenized with the dilute phosphoric acid using a spatula. The homogenized mixture was dried in a vacuum drying cabinet at 80° C. for 8 h and then (after heating time 4 h) calcined under air in a muffle furnace at 500° C. for 4 h.

The BET surface area of the resulting phosphorus-impregnated spall was 283 m$^2$/g.
Elemental analysis:
Si: 22.8 g/100 g
Al: 17.6 g/100 g
P: 3.7 g/100 g

Comparative Example 3

Preparation of an Extrudate Comprising Mg-ZSM-5

H-ZSM-5 (ZEO-cat PZ2-100 H from Zeochem) with Si/Al=50 powder was spray impregnated with a magnesium nitrate solution. In the course of this spray impregnation, unlike in the shell impregnation (comparative example 2), spraying was effected to 90% of the water absorption. The amount of Mg weighed in was such that the powder after the calcination comprises 4% by weight of Mg. For impregnation, 58.7 g of zeolite powder were introduced into a round-bottom flask and placed in a rotary evaporator. 43.9 g of magnesium nitrate were dissolved in water while heating, and made up to 54 ml of total liquid with dist. water. The resulting magnesium nitrate solution was introduced into a dropping funnel, and sprayed gradually onto the powder through a glass spray nozzle flooded with 100 l/h of N$_2$ while rotating. At regular intervals during this time, the flask was detached and shaken by hand, in order to achieve homogeneous distribution. On completion of addition of the magnesium nitrate solution, the powder was rotated further for 10 min. Subsequently, the powder was dried at 120° C. in a quartz rotary sphere flask for 16 h, after a heating time of 4 h the powder was then calcined at 500° C. under air (20 l/h) for 4 h, and the calcined powder was subsequently ground to a small size with the aid of an analytical mill and sieved through a sieve having a mesh size of 1 mm.

The BET surface area of the resulting magnesium-impregnated zeolite was BET 303 m$^2$/g.
Elemental analysis:
Mg: 3.7 g/100 g The Mg-ZSM-5 powder prepared by spray impregnation was further processed with pseudoboehmite (Pural SB; Sasol) as a binder to give extrudates. The starting weights were selected such that the zeolite/binder ratio in the calcined extrudate corresponds to 60:40. For this purpose, 58.7 g of zeolite and 50.7 g of pseudoboehmite (Pural SB; Sasol) were weighed in, mixed, admixed with dilute formic acid (1.5 g of formic acid in 20 ml of water) and processed with 38 ml of water to give a homogeneous material. The viscosity of the homogenized mixture measured with a curdmeter ("Curd Meter max ME-500" (from K.K. Itec Techno Engineering) was 1.633×10$^4$ N/m$^2$. The kneaded material was forced with the aid of an extrudate press through a 2.5 mm die at approx. 110 bar. Subsequently, the resulting extrudates were dried in a drying cabinet at 120° C. for 16 h and (after heating time 4 h) calcined in a muffle furnace at 500° C. for 4 h, and the calcined extrudates were processed in a sieving machine with 2 steel balls (diameter approx. 2 cm, 258 g/ball) to give 1.6-2 mm spall.

The BET surface area of the resulting spall was 291 m$^2$/g.
Elemental analysis:
Si: 24.5 g/100 g
Al: 19.0 g/100 g
Mg: 2.3 g/100 g
Na: 0.04 g/100 g

Example 1

Preparation of a Phosphorus-Treated Extrudate Comprising Mg-ZSM-5

According to the preparation method of comparative example 2, 10 g of the Mg-ZSM-5/Al$_2$O$_3$ spall from comparative example 3 were impregnated with an aqueous phosphoric acid solution (1.6 g of 85% H$_3$PO$_4$ made up to 5 ml with H$_2$O), dried and calcined.

The BET surface area of the resulting phosphorus-impregnated spall was 189 m$^2$/g.
Elemental analysis:
Si: 22.0 g/100 g
Al: 17.8 g/100 g
Mg: 2.1 g/100 g
Na: 0.03 g/100 g
P: 3.8 g/100 g The distribution of phosphorus in the extrudate was analyzed by analytical electron microscopy (EDXS). This showed that, surprisingly, the phosphorus concentration in the binder was approx. 9% by weight, whereas a phosphorus concentration of only approx. 1% by weight was measured in the zeolitic material. Thus, it has been found that, surprisingly, an extrudate prepared according to the present invention has a much higher phosphorus concentration in the binder matrix than in the zeolitic material present therein, even though the extrudate is impregnated in a way that would be expected to lead to a homogeneous distribution of phosphorus both in the binder matrix and in the zeolitic material.

The extrudate was also analyzed by x-ray powder diffractometry. FIG. 3 shows a section of the x-ray diffractogram of a sample of the extrudate in which the reflections of the zeolitic material ZSM-5, which is of the MFI structure type, are clearly evident, as shown by a comparison with the line spectrum of ZSM-5 which has additionally been included in the x-ray diffractogram. In contrast, it can be clearly inferred from the diffractogram that no AlPO$_4$ is present in the sample (see lines marked with "*" in FIG. 3). Thus, it has been found that, more particularly, no aluminum phosphate forms in the course of calcination of the phosphorus-impregnated alumina binder during the preparation process.

Example 2

Preparation of an Extrudate Comprising Mg-ZSM-5 and Phosphoric Acid

Mg-ZSM-5 powder produced by spray impregnation from comparative example 3 was processed further with pseudoboehmite (Pural SB; Sasol) as a binder to give extrudates. The starting weights were selected such that the zeolite/binder ratio in the calcined extrudate corresponds to 60:40. For this purpose, 115 g of zeolite and 105 g of pseudoboehmite (Pural SB; Sasol) were weighed in, mixed, admixed with 15.2 g of phosphoric acid (85%; Sigma-Aldrich), and processed with 5.75 g of Walocel and 130 ml of water to give a homogeneous material. The kneading material was pressed with the aid of an extrudate press through a 2.5 mm die at approx. 60 bar. Subsequently, these extrudates were dried at 120° C. in a drying cabinet for 16 h, calcined in a muffle furnace at 500° C. for 4 h (heating time 4 h) and processed in a sieving machine with 2 steel balls (diameter approx. 2 cm, 258 g/ball) to give 1.6-2 mm spall.

The BET surface area of the spall obtained was 265 m$^2$/g.
Elemental analysis:
Si: 22.9 g/100 g
Al: 19.9 g/100 g
Mg: 2.1 g/100 g
P: 1.8 g/100 g Example 3

Comparative Tests in the Methanol-to-Propylene/Butylene Process (MT3/4 Process)

The catalysts prepared in comparative examples 1 to 3 and in examples 1 and 2 (in each case 2 g) were mixed with silicon carbide (in each case 23 g) and installed in a continuously operated, electrically heated tubular reactor. Upstream of the test reactor, methanol vapor was produced to give a gas stream comprising 75% by volume of methanol and 25% by volume of N$_2$, which was converted to dimethyl ether by means of a preliminary reactor charged with 34 ml of alumina spall at 275° C. and an (absolute) pressure of 1-2 bar. The stream comprising dimethyl ether was then passed into the tubular reactor, and converted therein at a temperature of 450 to 500° C., a WHSV (=weight hourly space velocity) of 6 h$^{-1}$ based on methanol and an (absolute) pressure of 1 to 2 bar, and the reaction parameters were maintained over the entire run time. Downstream of the tubular reactor, the gaseous product mixture was analyzed by on-line chromatography.

The results achieved in the MT3/4 process for the catalysts according to comparative examples 1 to 3 and according to examples 1 and 2 with respect to the selectivities are shown in table 1, these reproducing the average selectivities during the run time of the catalyst in which the conversion of methanol was 97% or more. The results of the on-line chromatography analysis of comparative example 3 and of example 1 are each depicted in FIGS. 1 and 2.

TABLE 1

Average selectivities at a methanol conversion of >97%.

|  | Comparative ex. 1 | Comparative ex. 2 | Comparative ex. 3 | Ex. 1 | Ex. 2 |
|---|---|---|---|---|---|
| Service life [h] | 33 | 23 | 85 | 113 | 200 |
| WHSV [h$^{-1}$] | 6 | 6 | 6 | 6 | 6 |
| Selectivity [%]: |  |  |  |  |  |
| ethylene | 9 | 10 | 9 | 9 | 7 |
| propylene | 23 | 25 | 35 | 36 | 38 |
| butylene | 15 | 15 | 25 | 26 | 28 |
| C$_4$ paraffins | 9 | 8 | 3 | 3 | 3 |
| C$_{5+}$ (mixture) | 19 | 19 | 18 | 19 | 17 |
| aromatics | 17 | 15 | 6 | 5 | 5 |
| ethane, propane | 5 | 6 | 2 | 1 | 1 |
| methane | 2 | 1 | 2 | 1 | 1 |

As can be inferred from the values in table 1, it has been found that, surprisingly, the specific use of a combination of a phosphorus-comprising metal oxide with an alkaline earth metal-comprising zeolite leads to a surprisingly long service life of the catalyst for which a conversion of methanol of more than 97% can be maintained. As a comparison of the catalysts with and without phosphorus from comparative examples 1 and 2 shows, the service life of the catalyst with phosphorus from comparative example 2 is substantially reduced compared to the catalyst from comparative example 1 without phosphorus, whereas, in the inventive catalysts according to examples 1 and 2, the use of phosphorus, entirely contrary to expectation, leads to a substantial improvement in the service life of the catalyst, as shown by a comparison of the results for the inventive catalysts from examples 1 and 2 with the catalyst from comparative example 3 which has been prepared without phosphorus. In addition, it has also been found that, surprisingly, the inventive catalyst also brings about a rise in the selectivity toward the C$_3$ and C$_4$ olefins propylene and butylene compared to the comparative examples without alkaline earth metal and/or without phosphorus. Due to the aforementioned surprising effects of the catalyst according to the present invention from examples 1 and 2, it was all the more unexpected that this also brings about a considerable decrease in the unwanted by-products and especially methane in the MT3/4 process. This surprising effect is clearly evident especially by a comparison of the results of the on-line chromatography analysis of comparative example 3 and example 1 in FIGS. 1 and 2. Thus, a constant and significant increase is evident in the profile of evolution of methane as a by-product in comparative example 3 in FIG. 1 with increasing run time, whereas the increase in methane formation over the entire run time of the catalyst from example 1 is only extremely weak in comparison thereto (see FIG. 2).

Furthermore, it has been found that, surprisingly, the inventive catalyst according to example 2, the preparation of which involved introducing phosphorus in the form of phosphoric acid for extrusion of the zeolite and the binder, showed a considerable gain in service life compared to the catalyst according to example 1, and a further improvement in selectivity for C$_3$ and O$_4$ olefins. These further improvements are all the more advantageous in that the catalyst is prepared by a simplified process in which there is no additional impregnation of the finished extrudate with a phosphorus-comprising solution as in example 1. Thus, not only a highly efficient catalyst but also a particularly efficient preparation are provided by the process described in example 2.

Based on these unexpected effects which can be brought about by the unexpected synergy of doping with alkaline earth metal and with phosphorus according to the present invention, a catalyst is thus provided for the conversion of oxygenates to olefins which, as has been shown by the test results in the MT3/4 process according to example 3, not only enables significantly longer service lives, but also shows an increase in selectivity with respect to C$_3$ and C$_4$ olefins, and especially also enables a considerable reduction in by-product formation, especially of methane.

PRIOR ART DOCUMENTS CITED

DD 238733 A1
McIntosh et al. in Applied Catalysis 1983, 6, p. 307-314
Lee et al. in Applied Catalysis A 2010, 374, p, 18-25
Freiding et al. in Applied Catalysis A 2007, 328, p. 210-218
U.S. Pat. No. 4,049,573
Goryainova et al. in Petroleum Chemistry 2011, vol. 51, no. 3, p. 169-173
Ciambelli et al. "Acid-base catalysis in the conversion of methanol to olefins over Mg-modified ZSM-5 zeolite", Successful Design of Catalysts, Elsevier Science Publishers B.V., Amsterdam, 1988, p. 239-246
Okado et al. in Applied Catalysis 1988, 41, p. 121-135
WO 2012/123556 A1
WO 2012/123557 A1
WO 2012/123558 A1

The invention claimed is:

1. A catalyst for the conversion of oxygenates to olefins, wherein the catalyst comprises one or more zeolites of the MFI, MEL and/or MWW structure type and particles of one or more metal oxides, the one or more zeolites of the MFI, MEL and/or MWW structure type comprising one or more alkaline earth metals including Mg, and the particles of the one or more metal oxides comprising phosphorus, the phosphorus being present at least partly in oxidic form,
wherein the one or more metal oxides are selected from the group consisting of alumina, aluminum-titanium mixed oxides, aluminum-zirconium mixed oxides, aluminum-lanthanum mixed oxides, aluminum-zirconium-lanthanum mixed oxides, and mixtures of two or more thereof, and the particles of the one or more metal oxides are present in a range from 0.5 to 10% by weight, based on the total weight of the zeolites of the MFI, MEL and/or MWW structure type, and calculated as the element, and
the one or more alkaline earth metals are present in a range from 0.5 to 5% by weight, based on the total amount of the one or more zeolites of the MFI, MEL and/or MWW structure type, and calculated as the metal.

2. The catalyst according to claim 1, wherein the one or more zeolites of the MFI, MEL and/or MWW structure type comprise phosphorus, the phosphorus being present at least partly in oxidic form.

3. The catalyst according to claim 1, wherein the one or more zeolites are of the MFI structure type.

4. The catalyst according to claim 1, wherein the zeolite:metal oxide weight ratio in the catalyst is in the range from 10:90 to 95:5.

5. The catalyst according to claim 1 in the form of a shaped body comprising a mixture of the one or more zeolites of the MFI, MEL and/or MWW structure type and of the particles of the one or more metal oxides.

6. A process for preparing a catalyst according to claim 5, comprising
(i) providing the one or more zeolites of the MFI, MEL and/or MWW structure type;
(ii) impregnating the one or more zeolites of the MFI, MEL and/or MWW structure type with a solution comprising the one or more alkaline earth metals;
(iii) optionally drying the one or more impregnated zeolites obtained in (ii);
(iv) optionally calcining the one or more impregnated zeolites obtained in (ii) or (iii);
(v) preparing a mixture comprising the one or more impregnated and optionally dried and/or calcined zeolites of the MFI, MEL and/or MWW structure type, one or more solvents and particles of the one or more metal oxides and/or precursor compounds of the one or more particles of the one or more metal oxides;
(vi) homogenizing the mixture obtained in (v);
(vii) extruding the homogenized mixture obtained in (vi);
(viii) optionally drying the extrudate obtained in (vii);
(ix) optionally calcining the extrudate obtained in (vii) or (viii);
(x) impregnating the optionally dried and/or calcined extrudate with a phosphorus-comprising solution;
(xi) optionally drying the impregnated extrudate obtained in (x);
(xii) optionally calcining the extrudate obtained in (x) or (xi).

7. A process for preparing a catalyst according to claim 5, comprising
(i) providing the one or more zeolites of the MFI, MEL and/or MWW structure type;
(ii) impregnating the one or more zeolites of the MFI, MEL and/or MWW structure type with a solution comprising the one or more alkaline earth metals;
(iii) optionally drying the one or more impregnated zeolites obtained in (ii);
(iv) optionally calcining the one or more impregnated zeolites obtained in (ii) or (iii);
(v.1) preparing a mixture comprising the one or more impregnated and optionally dried and/or calcined zeolites of the MFI, MEL and/or MWW structure type and particles of the one or more metal oxides and/or precursor compounds of the one or more particles of the one or more metal oxides;
(v.2) admixing the mixture obtained in (v.1) with a phosphorus-comprising solution;
(v.3) mixing the mixture obtained in (v.2) with one or more solvents;
(vi) homogenizing the mixture obtained in (v.3);
(vii) extruding the homogenized mixture obtained in (vi);
(viii) optionally drying the extrudate obtained in (vii); and
(ix) optionally calcining the extrudate obtained in (vii) or (viii).

8. The process according to claim 6, wherein the impregnating in (ii) or the drying in (iii) or the calcining in (iv) is followed by bringing the one or more impregnated zeolites of the MFI, MEL and/or MWW structure type to a particle size $D_{50}$ in the range from 5 to 1000 µm.

9. The process according to claim 6, wherein the drying in (iii), (viii) and/or (xi) is effected at a temperature in the range from 50 to 220° C.

10. The process according to claim 6, wherein the calcining in (iv), (ix) and/or (xii) is effected at a temperature in the range from 300 to 850° C.

11. The process according to claim 6, wherein the solution used in (ii) and/or (x) and/or the mixture prepared in (v) comprises one or more solvents selected from the group consisting of
a. alcohols,
b. water,
c. mixtures of two or more alcohols, and
d. mixtures of water and one or more alcohols.

12. A catalyst for the conversion of oxygenates to olefins, obtained by the process according to claim 6.

13. A process for converting oxygenates to olefins, comprising:
(1) providing a gas stream comprising one or more oxygenates; and
(2) contacting the gas stream with the catalyst according to claim 1.

14. The process according to claim 13, wherein the gas stream according to (1) comprises one or more oxygenates selected from the group consisting of aliphatic alcohols, ethers, carbonyl compounds and mixtures of two or more thereof.

15. The process according to claim 13, wherein the content of oxygenates in the gas stream according to (1) is in the range from 30 to 100% by volume based on the total volume.

16. The process according to claim 13, wherein the water content in the gas stream according to (1) is in the range from 5 to 60% by volume based on the total volume.

17. The process according to claim 13, wherein the contacting according to (2) is effected at a temperature in the range from 200 to 700° C.

18. The process according to claim 13, wherein the contacting according to (2) is effected at a pressure in the range from 0.1 to 10 bar.

19. The process according to claim 13, wherein the process is a continuous process.

20. The process according to claim 19, in which the space velocity in the contacting according to (2) is in the range from 0.5 to 50 h$^{-1}$.

21. The process according to claim 20, in which the service life of the catalyst during which the continuous process is performed without interruption is in the range from 40 to 300 h.

22. The catalyst according to claim 1, wherein the catalyst does not include any significant amounts of calcium.

* * * * *